United States Patent

Adams et al.

(10) Patent No.: US 9,488,620 B2
(45) Date of Patent: Nov. 8, 2016

(54) WEAK BOND DETECTION

(75) Inventors: Douglas E. Adams, West Lafayette, IN (US); Nathan D. Sharp, West Lafayette, IN (US); Ronald Sterkenburg, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 357 days.

(21) Appl. No.: 14/004,594

(22) PCT Filed: Mar. 15, 2012

(86) PCT No.: PCT/US2012/029243

§ 371 (c)(1),
(2), (4) Date: Nov. 5, 2013

(87) PCT Pub. No.: WO2012/125837

PCT Pub. Date: Sep. 20, 2012

(65) Prior Publication Data

US 2014/0047922 A1 Feb. 20, 2014

Related U.S. Application Data

(60) Provisional application No. 61/452,877, filed on Mar. 15, 2011.

(51) Int. Cl.
*G01N 29/11* (2006.01)
*G01M 7/02* (2006.01)
(Continued)

(52) U.S. Cl.
CPC .............. *G01N 29/11* (2013.01); *G01M 7/025* (2013.01); *G01N 3/32* (2013.01); *G01N 19/04* (2013.01); *G01N 29/045* (2013.01); *G01N 29/46* (2013.01); *G01N 2291/02491* (2013.01)

(58) Field of Classification Search
CPC ......... G01M 7/025; G01N 3/32; G01N 3/34; G01N 19/04; G01N 29/045; G01N 29/46; G01N 29/11
USPC .................................. 73/588, 579, 582, 573
See application file for complete search history.

(56) References Cited

U.S. PATENT DOCUMENTS 4,519,245 A * 5/1985 Evans .............................. 73/579
4,567,764 A * 2/1986 Jamison et al. ................. 73/588
(Continued)

FOREIGN PATENT DOCUMENTS

WO 0068654 11/2000
WO 0073781 12/2000
(Continued)

OTHER PUBLICATIONS

"Some comparisons for damage detection on structures using genetic algorithms and modal sensitivity method" by Gomes et al., 2007.*
(Continued)

*Primary Examiner* — Hezron E Williams
*Assistant Examiner* — Xin Zhong
(74) *Attorney, Agent, or Firm* — John V. Daniluck; Bingham Greenebaum Doll LLP

(57) ABSTRACT

Apparatuses and methods are disclosed for determining whether a structure of bonded layers includes locations where the layers are weakly bonded. Embodiments include evaluating the frequency response of the structure in response to vibrational inputs. Alternate embodiments include evaluating the non-linear response of the structure using a modal analysis. Further embodiments include obtaining the vibrational information with an accelerometer contacting the structure, while additional embodiments include exciting the structure with an impact force, which may be applied at multiple locations on the structure's surface. Still further embodiments include performing a MAC, COMAC, and/or FRF analysis. Still other embodiments include varying the amplitude of the input vibration. Additional embodiments locate the areas of weakened bonding. Still other embodiments include methods and apparatuses for simulating a laminated structure with defective bonding, such as kiss bonding.

27 Claims, 30 Drawing Sheets

(51) Int. Cl.
*G01N 3/32* (2006.01)
*G01N 19/04* (2006.01)
*G01N 29/04* (2006.01)
*G01N 29/46* (2006.01)

(56) References Cited

U.S. PATENT DOCUMENTS

| | | | |
|---|---|---|---|
| 4,884,223 A | 11/1989 | Ingle et al. | |
| 4,956,999 A * | 9/1990 | Bohannan et al. | 73/587 |
| 5,327,358 A * | 7/1994 | Stubbs | 702/36 |
| 5,408,305 A | 4/1995 | Webster et al. | |
| 5,410,405 A | 4/1995 | Schultz et al. | |
| 5,519,486 A | 5/1996 | Baird et al. | |
| 6,181,431 B1 | 1/2001 | Siu | |
| 6,490,047 B2 | 12/2002 | Siu | |
| 6,505,130 B1 | 1/2003 | Springer et al. | |
| 6,619,119 B1 | 9/2003 | Duggan et al. | |
| 6,915,217 B2 | 7/2005 | Springer et al. | |
| 7,073,384 B1 | 7/2006 | Donskoy et al. | |
| 7,146,846 B2 | 12/2006 | Mahaffey et al. | |
| 7,333,898 B2 | 2/2008 | Griess et al. | |
| 2002/0043109 A1 | 4/2002 | Siu | |
| 2005/0072234 A1* | 4/2005 | Zhu et al. | 73/579 |
| 2006/0215175 A1 | 9/2006 | Yacoubian | |
| 2009/0113994 A1 | 5/2009 | Walker et al. | |
| 2009/0168074 A1 | 7/2009 | Monchalin et al. | |
| 2010/0319456 A1* | 12/2010 | Ume et al. | 73/622 |
| 2011/0118994 A1* | 5/2011 | Georgeson et al. | 702/43 |

FOREIGN PATENT DOCUMENTS

| | | |
|---|---|---|
| WO | 0179831 | 10/2001 |
| WO | 2006125162 | 11/2006 |

OTHER PUBLICATIONS

"Parameter Estimation Using Sensor Fusion and Model Updating" by Kevin Francoforte, 2007.*
"Minimal-sensing, passive force identificationtechniques for a composite structural missile component" by Stites et al., 2009.*
"Conceptual Structural Identification Using Modal Test and Its Application on Nondestructive Evaluation" by Zongfen Zhang.*
International Search Report and Written Opinion issued in PCT/US2012/029243 Jul. 2, 2012.
International Preliminary Report on Patentability issued in PCT/US2012/029243 Sep. 26, 2013.
Stites, Nick, et al., "Minimal-sensing, passive force identification techniques for a composite structural missile component," Shock and Vibration, vol. 16, 2009, pp. 117-142.

* cited by examiner

Model shows modal vectors for weak bond not consistent with the rest of the panel Compare healthy and weak bond panel response for 5 different modes, look at coupling between weak bond and normal bond Shape of 1 of the 5 modes looked at (red area represents weak bond area $$MAC = \frac{(\{v_2\}^T \{v_1\})^2}{\{v_2\}^T\{v_2\} \{v_1\}^T\{v_1\}}$$

Weak bond panel shows less mode vector consistency than healthy panel

Use coordinate modal assurance criterion (COMAC) to determine which points on the panel are contributing to loss of consistency. Calculation is the same as the MAC except it is done for one location over all modes while MAC is done for one mode over several locations Calculate COMAC for 8 healthy and 8 weak bond locations Locations in the weak bond area show less consistency Conclusion: Weak bonds create a loss of consistency in modal vectors In the illustrated embodiment, four 8" x 8" carbon fiber panels were tested, Two which were undamaged, and two which had an approximate 2" x 2" Square area with synthesized damage (lower bond strength). Each panel was tap tested using the mini hammer (shown at left) at 484 (22x22) equally spaced points and measured at 3 points on the back side using uniaxial accelerometers.

Modal vectors for each test were obtained using CMIF method. The modal vectors were then matched up with all tests and the modes were compared across all tests.

Looking at the FRFs from the 8"x8" panels showed that there appeared to be differences in the modes between 150 and 650 Hz (see FIG. 18 for expanded view).

The COMAC for each point was obtained using all modes between 150 and 650 Hz (8 modes total), comparing the same panel but with the two different amplitude tests. The two points around the outside of the panel were not included since these points were very noisy. The plots above show the two undamaged 8" panels.

Damaged Panel Results
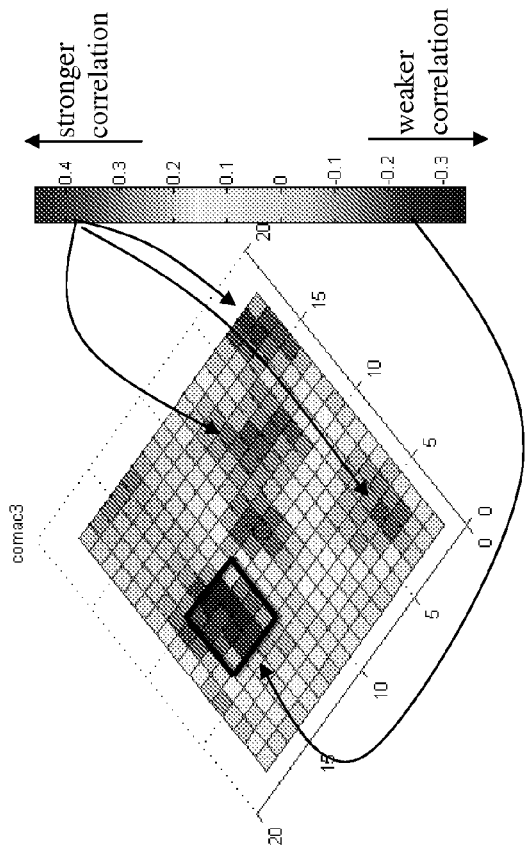
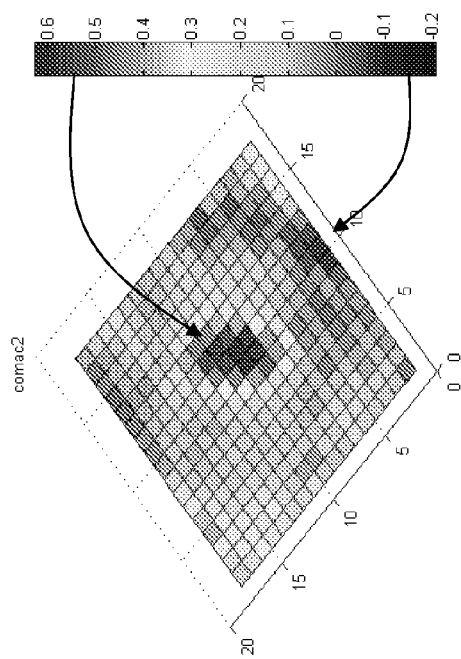
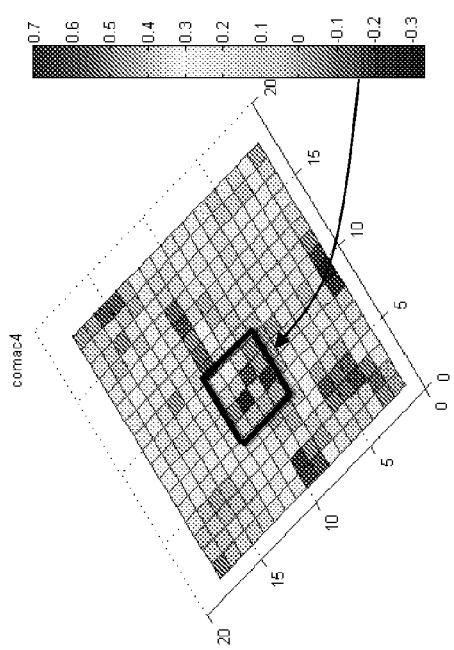
Top left plot shows an undamaged panel and the other two plots show the weak bond panels with a black square outlining the weak bond area.
FIG. 22

In order to mitigate the effects from the natural spatial differences in modal consistency of the mode shapes, a baseline can be created by creating a Bezier curve with the average of the baseline panels serving as the control points. If an automated system with more consistency is used, the baseline may be unnecessary.

WEAK BOND DETECTION

This application claims the benefit of U.S. Provisional Application No. 61/452,877, filed Mar. 15, 2011, the entirety of which is hereby incorporated herein by reference.

BACKGROUND

Future aircraft will be manufactured from composite materials including, for example, both glass and carbon fiber reinforced materials. Portions of these aircraft structures such as the fuselage can be large, in some cases reaching 40 ft in diameter. If these structures are or become defective, either by manufacturing inaccuracies or through damage, it may not be possible to replace these large sections of aircraft and they will need to be repaired in situ. Furthermore, several types of future aircraft and other types of systems such as composite ships will be constructed using adhesive joining techniques that can be susceptible to a weak bond, such as a "kiss bond," phenomena.

SUMMARY

Improper bonding of composite structures can result in close contact cracks under compressive stresses, called kissing bonds. These bond defects are difficult to detect using conventional inspection techniques (such as tap testing or local ultrasonic scanning) or advance inspection techniques (such as thermography testing) and can lead to local propagation of damage if the structure is subjected to crack opening stresses.

Embodiments of the present disclosure provide improved detection of weak bonds, for example, composite materials.

Various embodiments of the inventions shown herein have the ability to detect kiss bonds or other weakly bonded areas. Various embodiments are easier to use by an untrained inspector, and are also less expensive from an instrumentation standpoint when compared to ultrasonic sensing techniques.

Embodiments disclosed herein can serve as an inspection technique for detecting whether weak bonds are present in adhesive joints, after repairs are performed (such as determining whether a repair has been properly bonded to the host structure), or as a quality check during manufacturing. This ability can assist in satisfying the fail-safe or damage-tolerant allowables for the structural integrity of various types of future aircraft and other types of systems such as composite ships.

Embodiments identify weak bonds in composite materials using vibration measurements. A damage feature of the weak bond is extracted from the response of the input-output measurement that is a function of the structural path. This path exhibits local decoupling associated with the close contact cracks. Vibration measurements can be analyzed through a damage detection algorithm and, in some embodiments, compared to healthy sections, to detect locations where the structure is weakly bonded. Some embodiments detect locations of weak bonding to within 1 inch, while other embodiments detect locations of weak bonding to within 1 cm.

Embodiments evaluate the frequency response of a structure to determine the existence of weakly bonded areas. Certain embodiments employ modal analysis of the structure. Still further embodiments evaluate the non-linear response of the structure to vibrational excitation and evaluate the response utilizing a modal analysis.

A vibration based inspection technique can increase the ability to detect weak bonds in composite material repairs while decreasing inspection time. Some aspects of these methods of identification over conventional techniques include robust, objective damage detection methodology and a reduced requirement for specimen preparation and surface texture when compared to ultrasonic scanning.

Embodiments also include point vibration frequency response testing, for example, modal response testing, to detect weak bonds in composite repairs. Testing of simulated weak bond panels using embodiments of the present disclosure have verified the ability to identify the area of weak bonding and, in many embodiments, statistical analysis demonstrates no more than a four percent error rate. After gathering baseline data, a damage index algorithm demonstrated a substantial capability for detecting weak bonds.

Various embodiments of the present invention contemplate a weak bond detection device that is enclosed in a handheld device and takes no more than a few seconds to complete a detection reading.

Alternate embodiments provide a quick and sensitive way to identify weak bonds in composite repairs, which can be an integral step in composites becoming a more feasible and reliable material for construction of military and commercial aircraft.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein is not necessarily intended to address every object described herein, and each embodiment does not necessarily include each feature described. Other forms, embodiments, objects, advantages, benefits, features, and aspects of the present invention will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings. It is understood that such dimensions, or the relative scaling within a figure, are by way of example, and not to be construed as limiting.

FIG. 22 presents graphical representations of COMAC as a function of location on one healthy panel (Panel 2) and two damaged panels (Panels 3 and 4) according to an embodiment of the present invention.

DESCRIPTION OF THE ILLUSTRATED EMBODIMENTS

Figure 1:
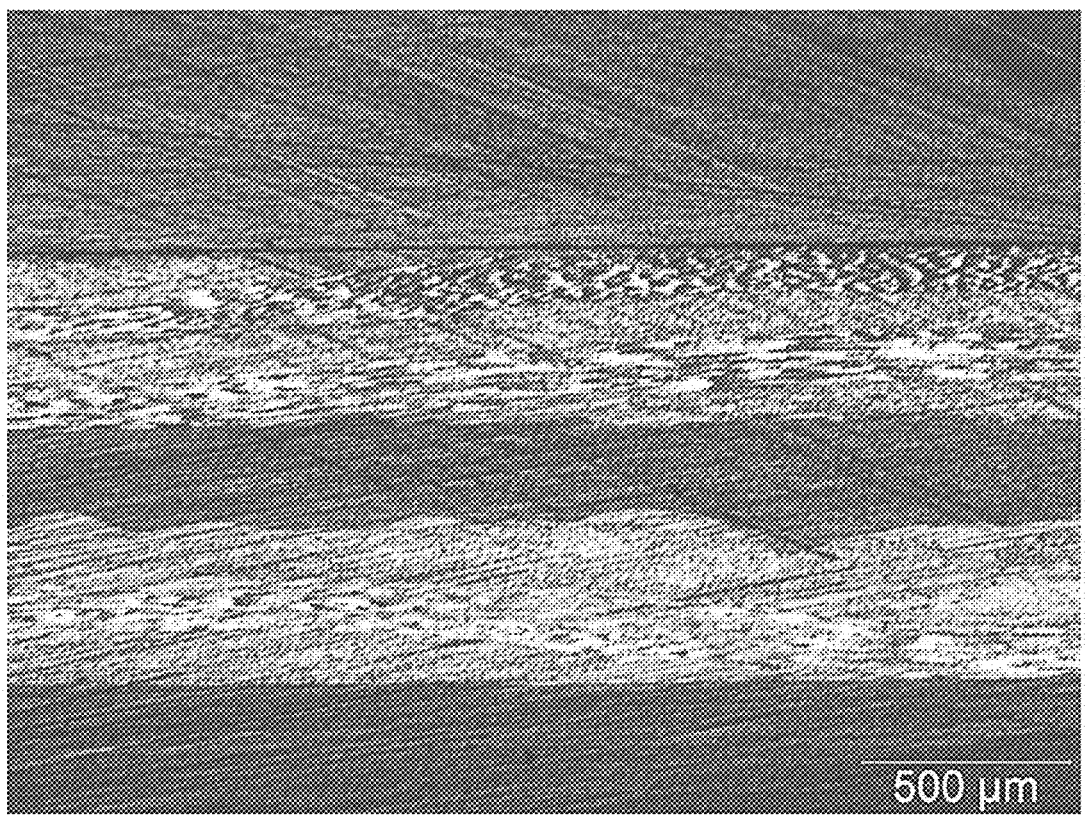
FIG. 1 is a microscopic view of the microstructure of the panel showing proper bonding.
Figure 2:
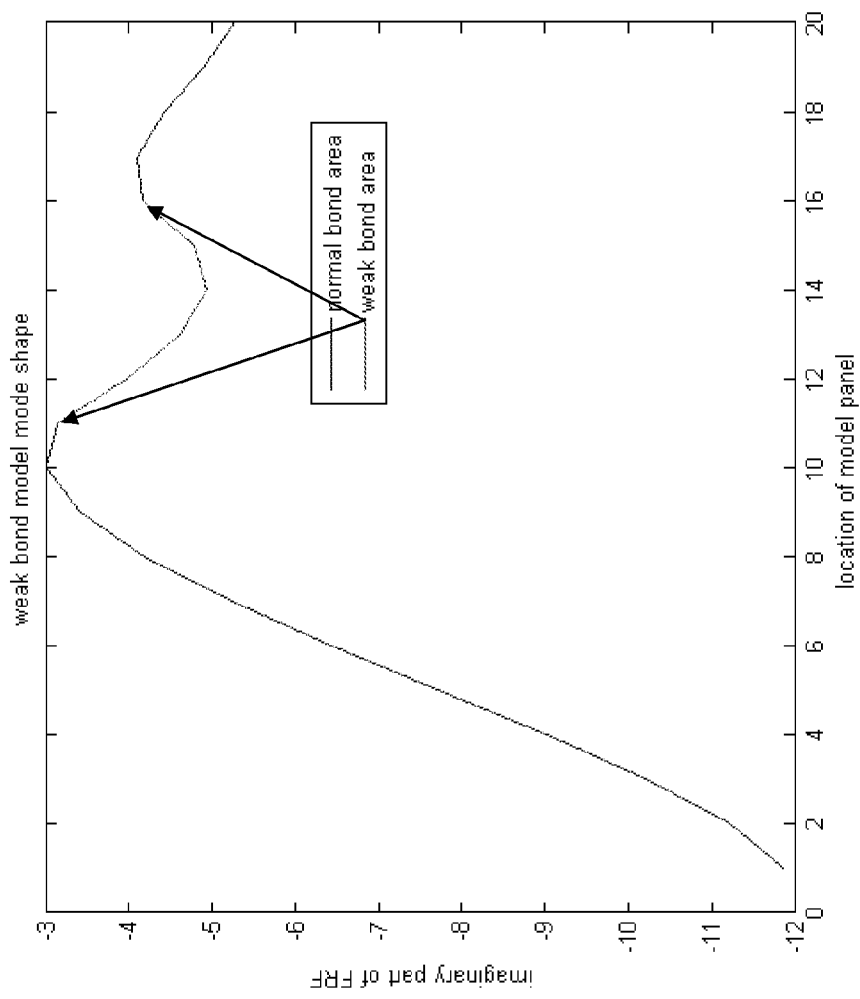
FIG. 2 is a graphical representation of the imaginary part of a frequency response function as a function of location on the model panel, showing a weak bond area from about location 11 to 16.

For the purposes of promoting an understanding of the principles of the invention, reference will now be made to the embodiments illustrated in the drawings and specific language will be used to describe the same. It will nevertheless be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to "advantages" provided by some embodiments of the present invention, other embodiments may not include those same advantages, or may include different advantages. Any advantages described herein are not to be construed as limiting to any of the claims.

Specific quantities (spatial dimensions, temperatures, pressures, times, force, resistance, current, voltage, concentrations, wavelengths, frequencies, heat transfer coefficients, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

The use of an N-series prefix for an element number (NXX.XX) refers to an element that is the same as the non-prefixed element (XX.XX), except as shown and described thereafter. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology.

A so-called "kissing" bond occurs in a composite material when the adhesive does not actually bond, but instead compressive stresses in the material create a mechanical bond, which has some weak sticking effects but very little strength. A kissing bond is one type of weak bonding that may occur between two bonded layers, such as laminated composites used in aircraft. The next generation of military helicopters is being designed to be made largely from composite materials. A major setback to using composite materials in military aircraft is the possibility of developing kissing bonds in the composite material during manufacturing or during a bonded repair procedure. These types of bonds are extremely difficult to detect by the standard composite inspection methods. Some success in kissing bond detection has been demonstrated by means of ultrasonic wave methods, but these methods are expensive, time consuming, and sensitive to the user's experience level. It is desirable to have an accurate inspection method that is both quick and portable as well as robust to the user's experience with nondestructive testing. Various embodiments pertaining to apparatus and methods for a vibration-based inspection method for composite repairs that has the potential to address these current issues are given below.

Since kissing bonds are difficult to create intentionally, and since it is difficult currently to detect kissing bonds and therefore difficult to verify that a kissing bond has been created, the bonds were simulated. This was done by using two different adhesives with different bonding strengths in the same composite panel. After the panel testing was successfully completed, the panels were analyzed to ensure that the epoxies bonded properly at the interface between the different types. This was done by cutting the panel in the area of interest, polishing the sample, and looking at the sample under a microscope to see the microstructure. This process was done on all four panels without any sign of separation of the plies or any other type of void. FIG. 1 shows one of the areas that was examined. The middle region of the figure is the bonded part of the panel and the figure shows proper bonding of the epoxies and the fibers. If there had been separation between the plies, there would have been a large lighter area from the air inside the void. This result confirms that the simulated kissing bond panels do indeed have the desired properties.

Figure 3:
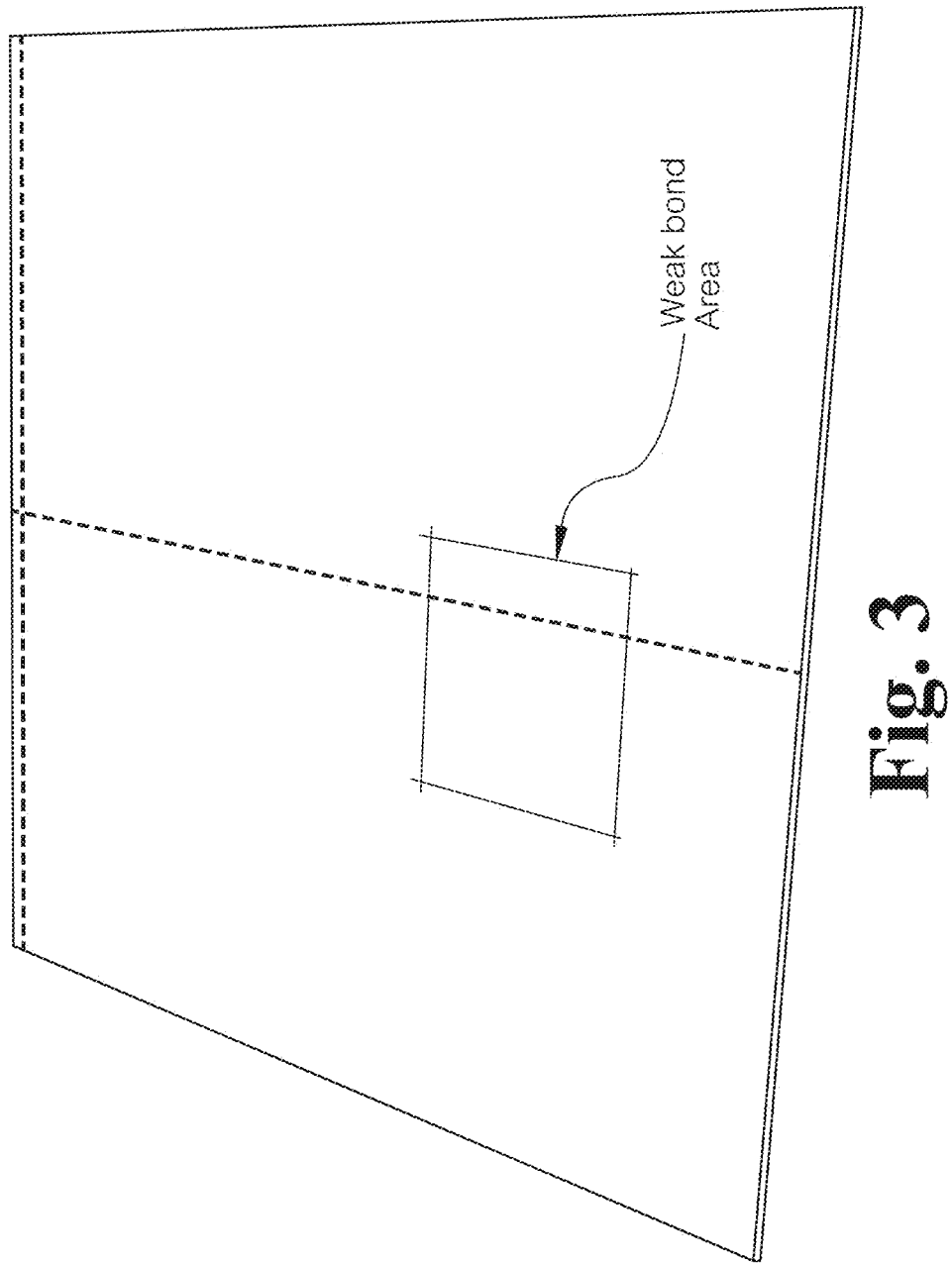
FIG. 3 is a photographic representation of an example of the composite kissing bond panels tested.

Four composite panels, 8"×8", were used for the testing. The fiber type for the panels was SGP196P. This fiber type was selected because it is of interest to aircraft manufacturers. Two different epoxies were used on the panels: the "normal" bond epoxy was rated at 5000 psi; and the "kissing" bond epoxy was rated at 2000 psi. The weaker epoxy was randomly placed in one two inch square area in each panel. Each panel was tested on a horizontal piece of foam that can be approximated as a free-free boundary condition. FIG. 3 shows one of the test panels laying on the foam with the weak bond area pointed out.

Figure 4:
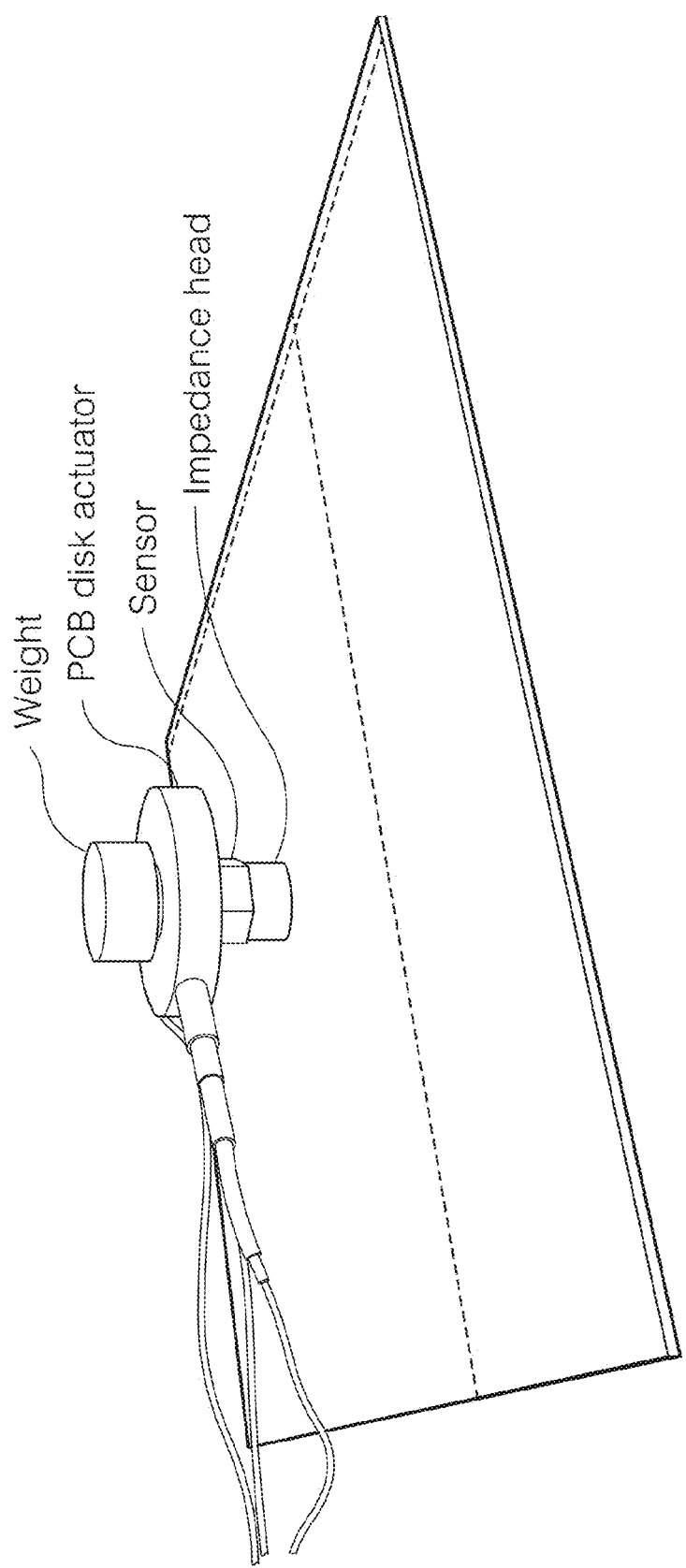
FIG. 4 is a photographic representation of an actuator and impedance head used to estimate driving point frequency response functions according to one embodiment of the present invention.

The panels were tested using a PCB piezoelectric disk actuator, model number 712A02. The actuator was threaded to a PCB 288D01 impedance head, which measured the force and acceleration perpendicular to the test panel. This type of driving point measurement can be used to calculate the compliance (displacement/force), mobility (velocity/force), or accelerance (acceleration/force) of the material as a function of frequency. A 100 gram mass was also threaded on top of the actuator to help transfer force into the panel. FIG. 4 shows an actuator and impedance head according to one embodiment placed on a panel in the testing configuration.

Because the kissing bond area in a material is not as strongly bonded as the healthy sections, it was hypothesized that if the material is excited with vibration energy the kissing bond area should cause the specimen to couple less to the transducer than the well-bonded areas of the panel. Therefore, if the frequency response of the material is analyzed in the region that has a kissing bond, there should be differences in the dynamic response in the form of shifting of peaks in frequency and amplitude and the possible disappearance of modal frequencies of vibration altogether. The driving point frequency response of the panel in the out-of-plane direction at several locations is obtained by roving the transducer that is pictured in FIG. 3. The frequency response function matrix, $H(j\omega)$, is then populated with these measurements, which each relate one input force to the material, $F(j\omega)$, to one output response acceleration from the material, $A(j\omega)$ through the relationship:

$$A(j\omega)_{m \times 1} = H(j\omega)_{m \times n} F(j\omega)_{n \times 1} \quad (1)$$

Figure 5:
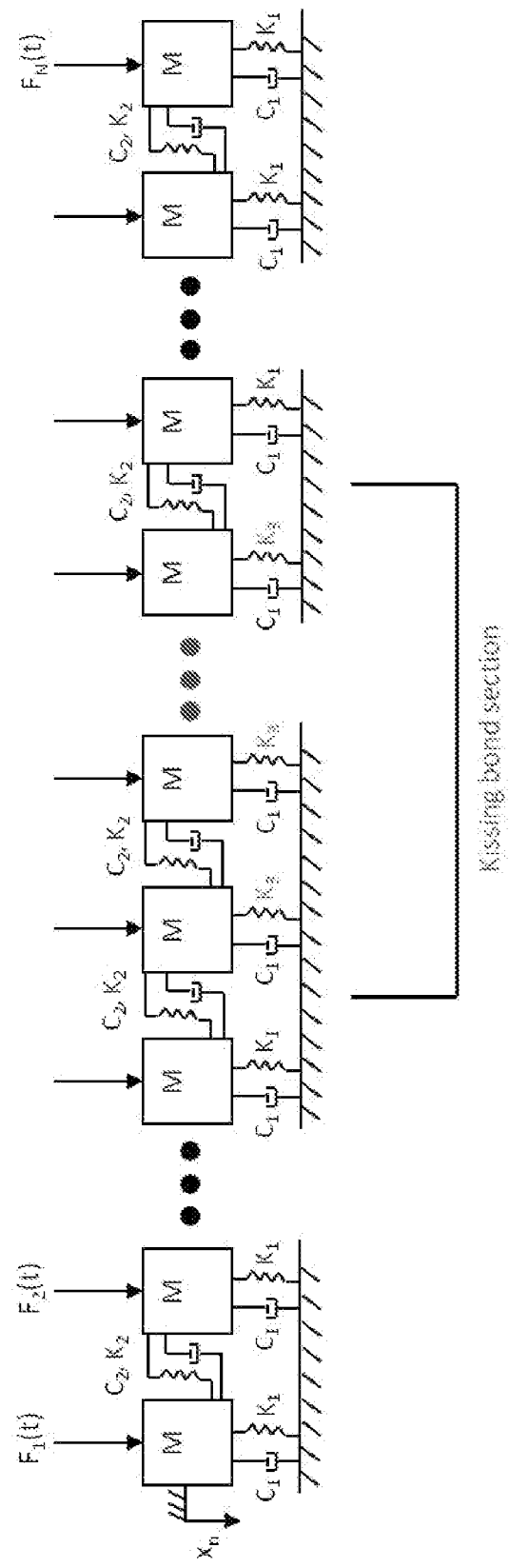
FIG. 5 is a schematic representation of a model of the kissing bond panels showing how the kissing bond was simulated.

A model was created to theoretically test the hypothesis that the kissing bond areas will respond to vibration energy through the shifting and/or loss of resonance frequencies in the frequency response measurement. The panel was modeled as a linear array of masses, where each mass represented the upper face sheet and was attached to ground with a spring and a damper. All of the masses were equal and each was assigned the same stiffness and damping relative to ground, except for the masses which were located in the kissing bond area. The kissing bond masses were assigned a lower stiffness because they were not as well bonded because of the compressive stresses. A stiffness reduction was used to represent the kiss bond area because it was hypothesized that the lower strength adhesive would result in residual stresses that could be modeled using such a stiffness reduction. The masses also were assigned a stiffness and damping between successive masses to represent the shear transfer of load in the panel through the composite action. FIG. 5 shows a schematic of the kissing bond panel model that was created.

Figure 6:
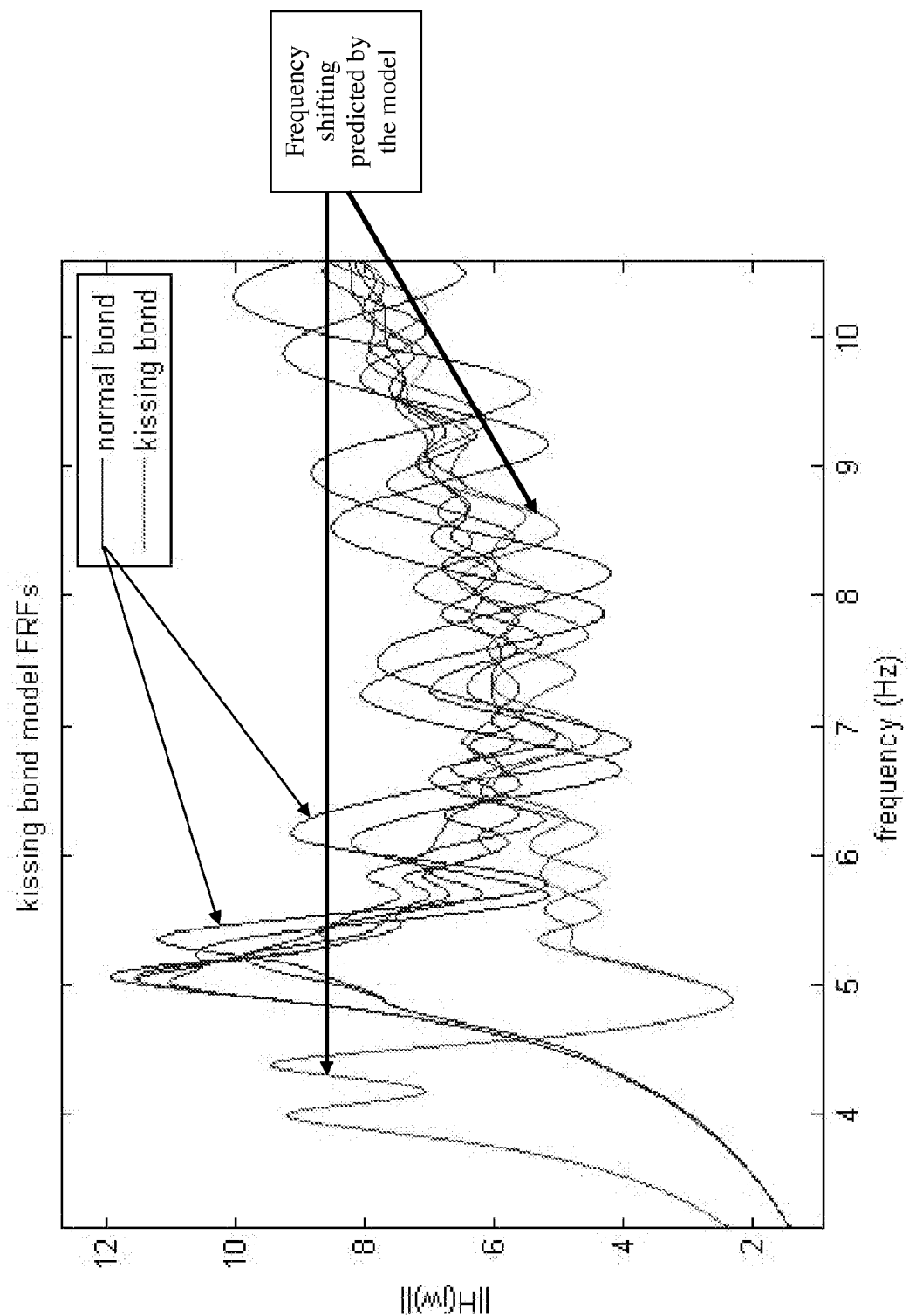
FIG. 6 is a graphical representation of the comparison FRF's for the modeled normal bond and kissing bond.

By using Equation (1) the FRF matrix [H] was calculated for this model and several FRF magnitudes were plotted to observe the difference in the frequency response between the low-shear bond strength (kissing bond) area and the normal bond strength area. FIG. 6 shows several normal frequency responses (blue) and two kissing bond frequency responses (red). The responses show a shift in the resonant peak in the kissing bond frequency responses when compared to the normal responses. This plot was created using a 100 degree of freedom (DOF) model with masses 20-40 being specified as weak bond areas. Two kissing bond responses and six normal bond responses were sampled and plotted.

Eight specified normal locations and three specified weak bond locations were created for each test panel. The locations were placed such that they were as similar as possible to each other (they were not exactly the same because the weak bond locations were randomly placed). The actuator was programmed to input a sine swept response that sweeps from 0-5000 Hz in two seconds. The data was then brought into MatLAB to estimate the frequency response using an $H_1$ frequency response estimator.

The FRF responses for each panel were estimated and then plotted on top of each other (strong bond plotted in blue, weak bond plotted in red) to verify that the weak bonds produce shifts in the resonance peaks.

Figure 7:
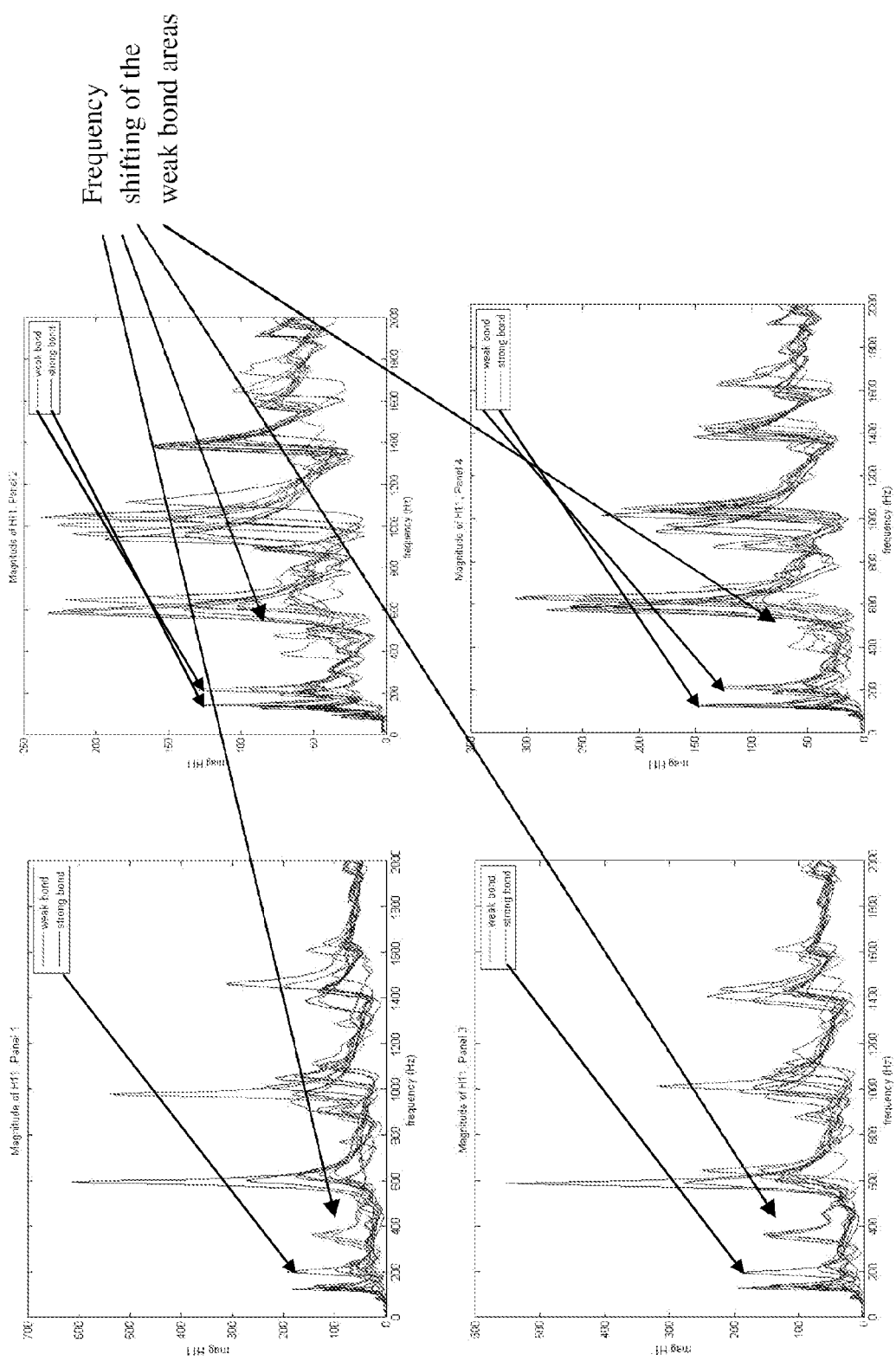
FIG. 7 shows graphical representations of measured FRF's of panel 1 (top left), panel 2 (top right), panel 3 (bottom left), and panel 4 (bottom right).
Figure 8:
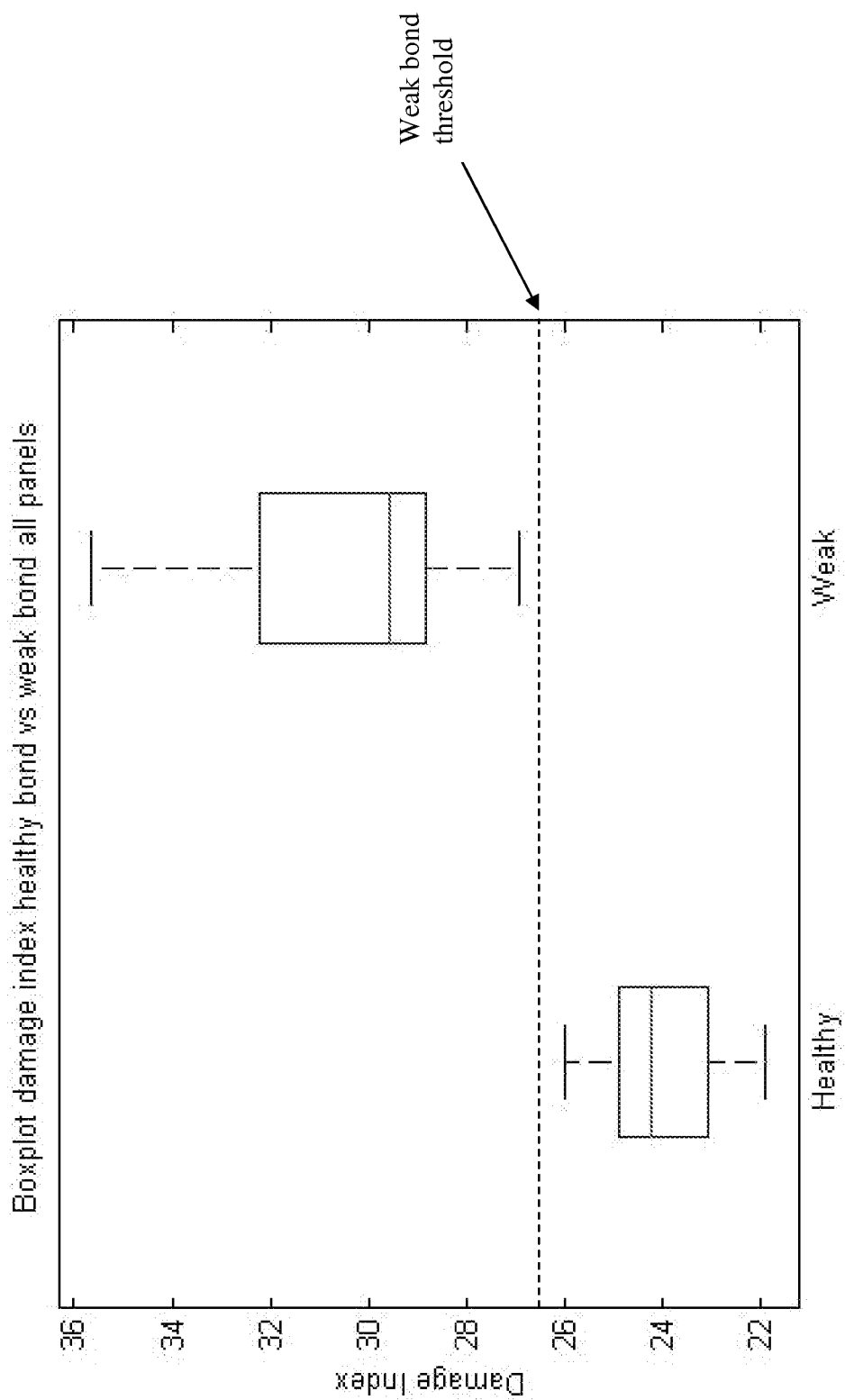
FIG. 8 shows a boxplot of damage index comparing the weak bond and healthy bond data with damage threshold shown.
Figure 9:
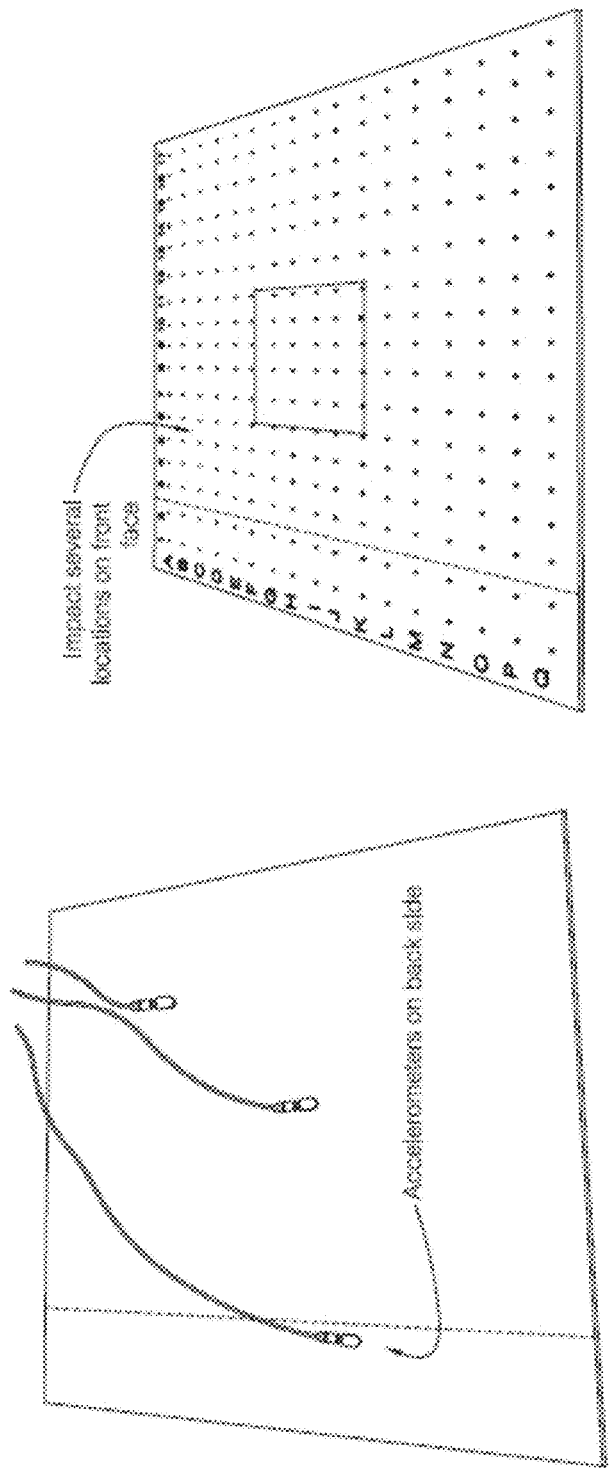
FIG. 9 presents photographic representations of a method according to another embodiment of the present invention in which a hammer is used to apply an impulse force to the structure, according to another embodiment of the present invention.
Figure 10:
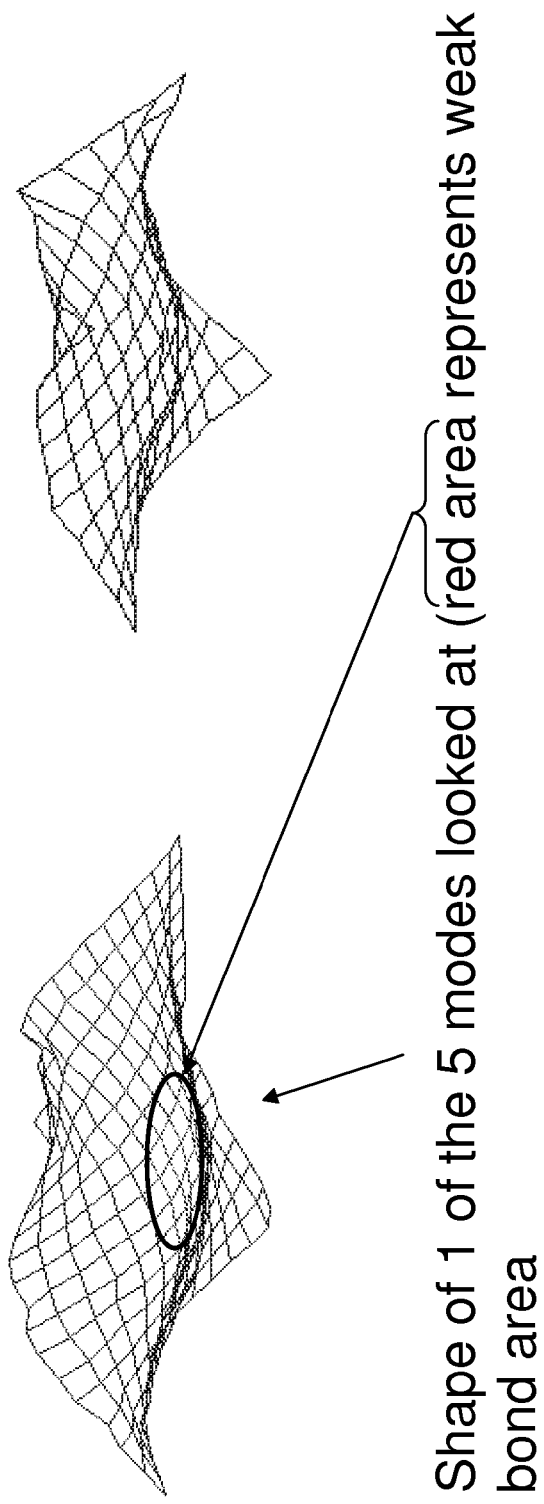
FIG. 10 is graphical comparison and weak panel response for one of the mode shapes, showing a weak mode shape in the left wire image in the middle of the mesh.
Figure 11:
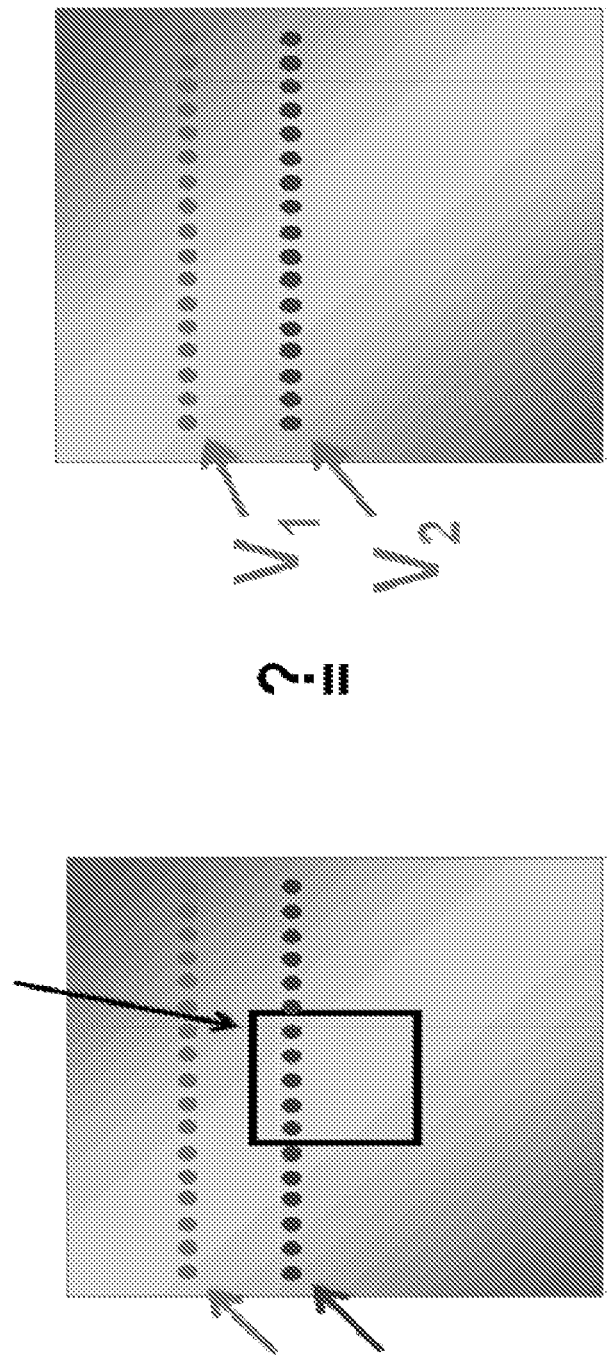
FIG. 11 is a graphical representation of a modal assurance criterion (MAC) according to another embodiment of the present invention.

FIG. 7 shows a shifting of the resonant peaks in the weak bond area as compared to the rest of the specimen. The frequency shifting phenomenon can be more clearly seen in panels 1 and 3 than in panels 2 and 4. It is possible that this is because of the different locations of the weak bond, but it should also be noted that all panels had a slight warp to them, creating residual stresses in the panels, which were most prevalent in the center. This slight, but noticeable, warp could possibly have affected the results for the weak bond testing in panels 2 and 4 more than in panels 1 and 3. Nevertheless, a noticeable difference in the results between weak bond and normal bond sections in all panels indicates that this procedure can still be effective even under imperfect conditions.

Panel 1 shows a pair of strong bond resident peaks at about 150 and 200 Hz. The weak bonds of panel 1 show a resonant frequency at about 380 Hz, a region in which the strong bonds of panel 1 had no substantial response. Similar results were obtained with panel 3.

In order to quantify the differences, the FRFs were broken in histograms of 250 Hz buckets and normalized by the total energy of the FRF to get the percent of the response in each bucket, $B_i$. Then the average of all responses was calculated for each panel as a baseline. A damage index, DI, was calculated by summing the ratio of each response to the baseline response (making sure to always produce a ratio that is bigger than 1). This damage index essentially is a measure of how much each response differs from the average response. The histogram buckets reduce the sensitivity of the damage index to natural variations in the response.

$$DI_m = \sum_{i=1}^{\text{\# of buckets}} \max\left[\frac{B_i}{B_{ave}}, \frac{B_{ave}}{B_i}\right] \quad (2)$$

A threshold was created using a statistical t-table such that 98 percent of all responses from healthy panels (+/−approximately 3σ) will fall below the threshold level. Using this threshold, the statistical analysis shows that 96 percent of all weak bonds will register above the threshold, leading to a 4 percent error. In the experiments, all of the measured data is on the correct side of the threshold, so it is likely that these error percentages are actually even smaller, but the small sample size (only 12 total weak bond measurements) does not allow for further characterization (the sample size was not increased beyond four panels due to the high cost of the panels and the time constraint on testing them). FIG. 7 below shows a box plot with the damage indices for all panels and the weak bond threshold, the box plot presenting information in a typical format.

The ability to identify weak bonds using this type of application is somewhat localized: the actuator should be directly on the affected area for the frequency shifting to appear. This is due to the need to adequately excite the bond material beneath the stiff ply material. The method is especially effective if the region of interest were small such as in an area with known bond lines. For example, repair patches could possibly be inspected using this technique to qualify the quality of the bond strength.

It should be noted that it is helpful to establish a baseline for this procedure to be applied. One potential application for this procedure is on repair patches of composite materials, and this ability to acquire adequate data for such a baseline signature is not problematic. Repairs of an identical host material should behave similarly. The panels that have been tested are not a simplification of the potential application, but are roughly equal in complexity.

Similar methods as the one described in this document have already been shown to be able to identify other types of damage to composite materials. This method would not be restricted solely to identifying kissing bonds but might also be used to ensure that no other type of defect has entered the repaired section.

Figure 12:
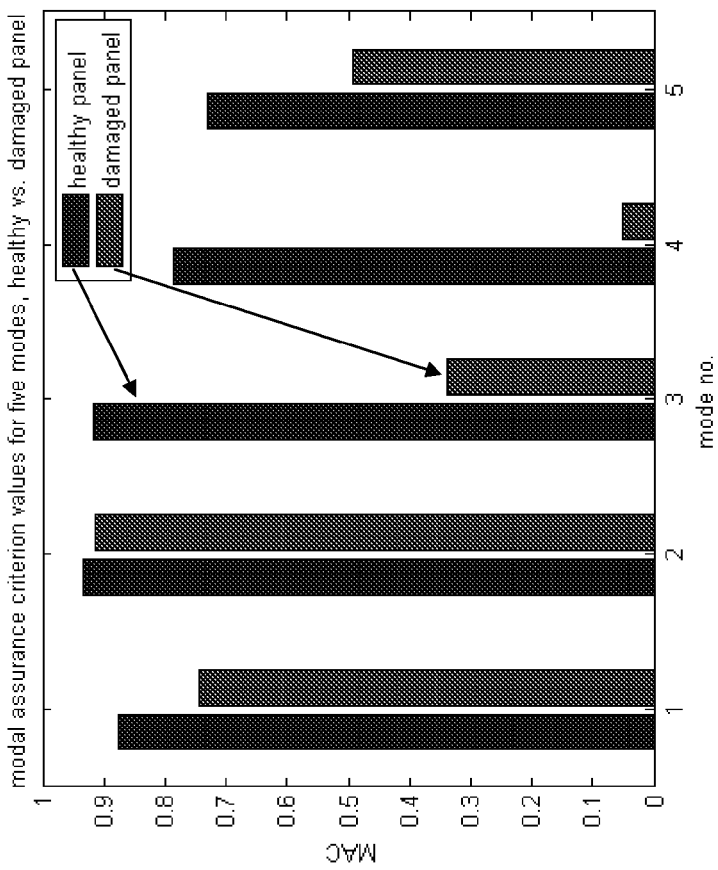
FIG. 12 shows an algorithm according to one embodiment of the present invention for computation of MAC (at the top of the figure); and test results showing the MAC as a function of mode number for both healthy and damaged panels.

Yet another embodiment of the present invention pertains to the use of a modal assurance criterion (MAC) that uses vibratory response of a composite panel to detect locations of inadequate bonding. The MAC procedure takes two rows of measurements at a certain mode (a specific frequency) and is a measure of how well the shapes match up at the mode. FIG. 12 shows the result of the MAC procedure, comparing a healthy panel to a damaged (or inadequately bonded) panel. FIG. 12 shows comparisons at five different modal shapes (the modal responses at five different frequency locations), with modes 3 and 4 showing the most deviation (the closer to 1 the number is, the better the shape matches, and the less likely it is that the panel shows damage). This is performed for healthy and weak bond panels. The MAC procedure can provide an indication as to whether or not a panel is damaged. However, by focusing on modal shapes, it does not necessarily provide enough information as to specific regions causing a lack of modal consistency between healthy and damaged bonded panels.

Figure 13:
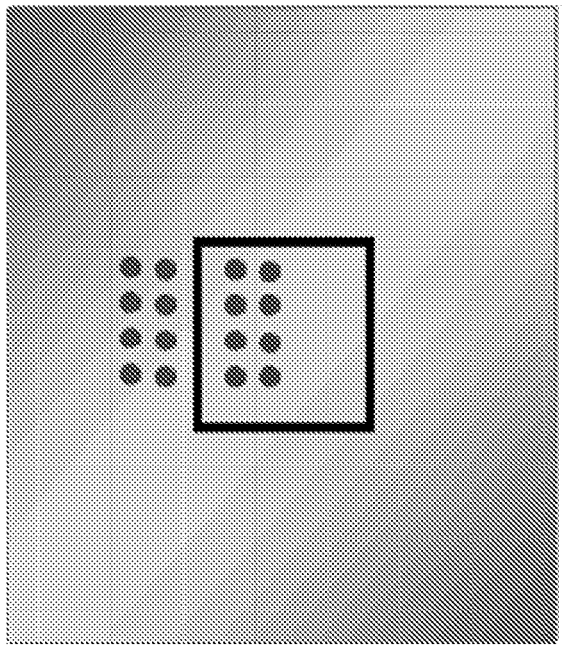
FIG. 13 is a representation of a coordinate modal assurance criterion (COMAC) according to one embodiment of the present invention.
Figure 14:
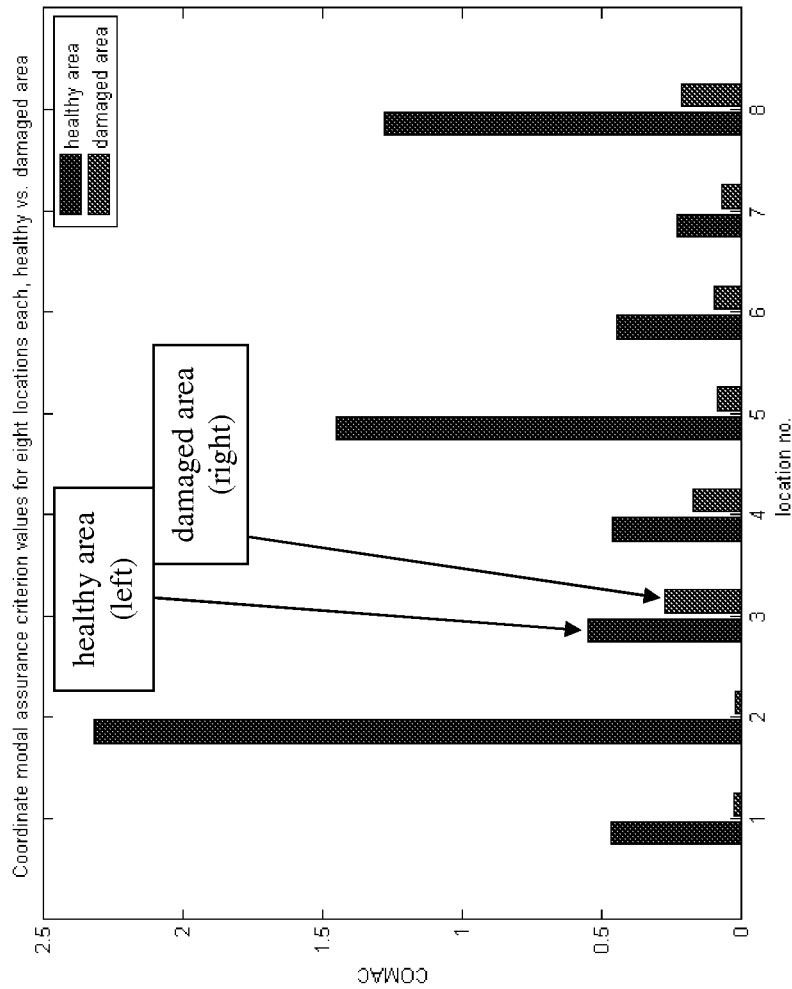
FIG. 14 presents a graphical representation of COMAC as a function of location number for both healthy and damaged areas, showing that weak bonds create a loss of consistency in modal vectors.

Yet another embodiment of the present invention processes vibratory information from a panel according to a coordinate modal assurance criterion (COMAC) to determine specific points on the panel that are most suspect of damage or weakness. In one embodiment, the COMAC procedure processes vibratory information about a particular point on the structure, comparing the response across all modes for a point on the panel being interrogated, as compared to the same point on a corresponding, known healthy structure. In yet another embodiment, the COMAC procedure is applied for points relatively close to one another on the same test panel. As best seen in FIG. 13, 16 points were selected in one area of a test panel. Eight points were known to be healthy (properly bonded), and the other 8 points were considered to be simulations of improper bonds. FIG. 14 shows a comparison of the 8 healthy points to the 8 weak points (using an algorithm similar to that shown at the top of FIG. 12, except modified to represent the vibratory response of individual points across a plurality of modes). It can be seen in the graph of FIG. 14 that the weekly bonded areas show very little consistency when all modes are considered.

One embodiment of the present invention pertains to apparatus and methods for the assessment of internal bonds in a laminate structure. In one embodiment the apparatus includes a housing that incorporates an accelerometer or other sensor for detecting vibrational response. The housing includes a handle for gripping by the user. In some embodiments, the housing further includes a source of excitation, such as a vibration exciter, whereas in other embodiments the source of excitation is a tapping device. An electronic controller within the housing provides a control signal to the source of actuation (which is powered by a portable battery). In addition, the electronic controller receives signals from the vibration sensor.

Both the vibration sensor and the source of actuation have external interfaces on the housing. The operator holds the housing by the handle and places the actuation source and the vibration sensor in contact with the panel to be tested. When this apparatus is placed by the user at a location in which the bond strength is to be determined, the operator pulls a trigger to command the electronic controller to begin the detection process. An actuation signal is sent to the source of excitation, which is already in contact with the surface, and which provides a mechanical input to the structure being interrogated (a vibratory input in some embodiments, a tapping or impulsive-type input in other embodiments, or a mix of both in other embodiments). At the same time, the electronic controller receives a signal from the vibration sensor. The vibration sensor, which is also in contact with surface to be interrogated, detects motion of the surface that results from the excitation from the source. The electronic controller in some embodiments further receives a signal from the source of excitation, from an accelerometer or other sensor capable of detecting the excitation being provided to the structure.

In some embodiments, the operator moves the handheld device to a plurality of different points on the structure. In some embodiments, the measurement points are predetermined with regards to their relative spacing. In other embodiments, the points are selected to surround a portion of the structure that has been repaired. In some embodiments, the predetermined spacing between points is provided by the operator as inputs to the electronic controller. These inputs may be provided by way of a keyboard in some embodiments, whereas in other embodiments the electronic controller instructs the operator as to the spacing between points. In yet other embodiments, the handheld device includes one or more tactile two dimensional position sensors that stay in contact with the surface as the operator moves from one point to another. The output of these position sensors create an electronic map within the electronic control that allows the computer to understand and account for the spacing of one point relative to another point. In yet other embodiments the tactile position sensors are three dimensional, further allowing the electronic controller to detect the curvature of the surface.

In yet other embodiments the handle and/or housing are spring loaded relative to the sensing and excitation end of the housing. In these embodiments, the distance from the handle to the sensing and excitation is variable across a length, such that one end of the housing is guided to fit within another portion of the housing. Preferably, the opposite ends of the housing are spring loaded apart. In such applications, the operator can place the sensing and excitation end against the surface to be interrogated, and lightly press on the housing so as to compress its length to a position between fully extended and fully retracted. In this manner, the operator places a normal load against the surface that is established by the spring constant and the amount of compression. Therefore, the surface pressure between the vibration sensor and the surface, and also the pressure between the source of excitation on the surface, is held within limits in order to enhance repeatability.

In some applications, the source of excitation is a vibrational source that operates within a predetermined frequency band. Therefore, when energized by the control signal from the electronic controller, the vibrational source places a vibrational input end of the structure such as a swept sine wave, random vibration, or other spectra. In some embodiments there is a load cell that is interposed between the end source of excitation and the surface such that the vibrational input to the surface can be measured as the source is actuated.

In yet other embodiments, the source of excitation is an impulsive-type tapping device. For example, the source of excitation can be a mechanical member that can be energized to move to a position in which it strikes the surface (such as a spring loaded electronic solenoid). Further, the operational end of the source of tapping excitation can include a load cell, such that the tapping source is similar in some respects to a calibrated hammer.

Figure 15:
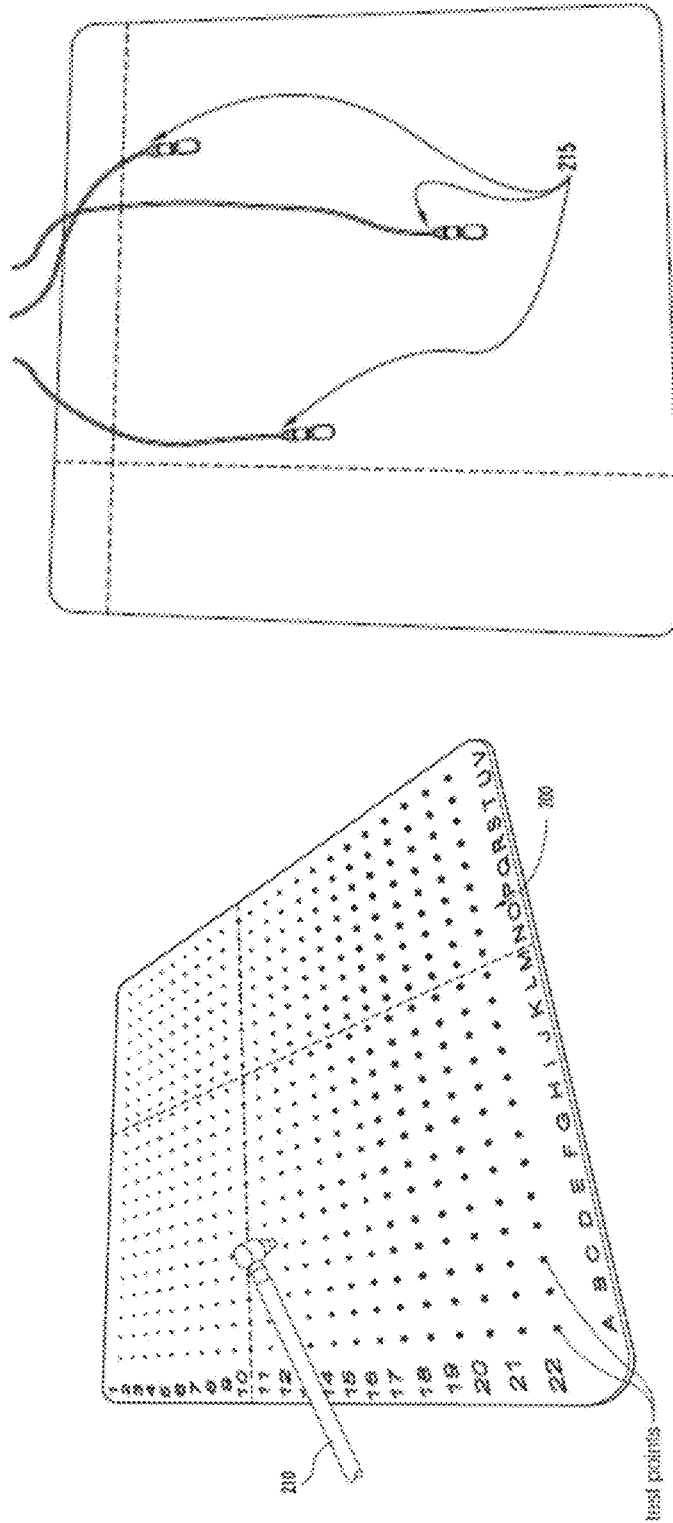
FIG. 15 is a photographic representation of a simulated damaged bond panel and a modal hammer according to one embodiment of the present invention.

FIG. 15 depicts methods and apparatuses for vibrating a structure with bonded layers, for example, laminated carbon fiber panel 200. In the illustrated embodiment an impacting device, such as the modal hammer 210 depicted in the front side view of the carbon fiber panel, is used to impact the bonded panel 200. (One example modal hammer is a PCB modal hammer model number 086E80). In one embodiment, the impacting device is used to impact the panel at multiple locations, such as at 484 equally spaced locations arranged in a 22×22 grid depicted on the front side of panel 200. In other embodiments, an automated device can be used to vibrate the panel, which can potentially roam over the panel and deliver precise frequency and amplitude vibrations to the panel.

One or more accelerometers 215 are placed in contact with the panel 200, and may be attached such as by using wax, adhesives, clamps, or other types of chemical or mechanical attachment. Accelerometers 215 detect panel vibrations at the locations at which the accelerometers 215 contact the panel 200. In the illustrated embodiment the accelerometers 215 are in contact with the back side of panel 200 and detect vibrations that have prorogated from the front side of panel 200 where the impacts occur to the back side of panel 200. However, in alternate embodiments, the one or more accelerometers to 215 may be placed on the same side of the panel 200 at which the vibrations are being applied to panel 200, while in still further embodiments some accelerometers may be on the front side while others are located on the back side of panel 200. Alternate embodiments also include generating vibrations within panel 200 at a single point, as well as impacting panel 200 at multiple irregularly spaced points. Accelerometers 215 are uni-axial (single axis) accelerometers, although other embodiments utilize multi-axial accelerometers (such as dual or triple axis).

Embodiments at the present invention also include methods and apparatuses for constructing a bonded structure with one or more locations of degraded bonding between layers, which can provide an accurate simulation of a damaged composite panel where delamination is incipient. In one embodiment, the bonding agent used to bond the two or more layers is applied in such a manner as to weaken the bonding in at least one location. To weaken the bond, another bonding agent can be applied to the location where weak bonding is to be simulated. The other bonding agent may interact with and affect the bonding capabilities of the proper bonding agent, or the alternate bonding agent may be the only bonding agent applied to the simulated area of impaired bonding. The proper bonding agent may also be applied in insufficient amounts (or not at all) to the areas where weak bonding is to be simulated.

In still further embodiments, hammer 210 applies vibrations of different amplitudes to panel 200. For example, in one embodiment hammer 210 impacts panel 200 with differing amounts of force, for example a first set of weaker impacts and a second set of stronger impact. The strong and weak impacts may be arranged such that a weak and strong impact occur at a single location, while other embodiments include using a weak impact at one location and a strong impact at another. In the embodiment illustrated in FIG. 15, a weak impact and a strong impact were applied to each of the 484 locations. The weak and the strong impacts were applied consistently, each of the weaker impacts being within 10% of a desired impact force (vibrational input amplitude) and each of the stronger impacts being 10% of a larger desired impact force (vibrational input amplitude). As such, the vibrational excitations of panel 200 were constrained to occur within two amplitude bands, one occurring at a higher amplitude than the other. Nevertheless, alternate embodiments of the present invention contemplate more than two vibrational excitation amplitudes and the application of vibrational amplitudes that are not necessarily of the same magnitude as other vibrational excitations.

Figure 16:
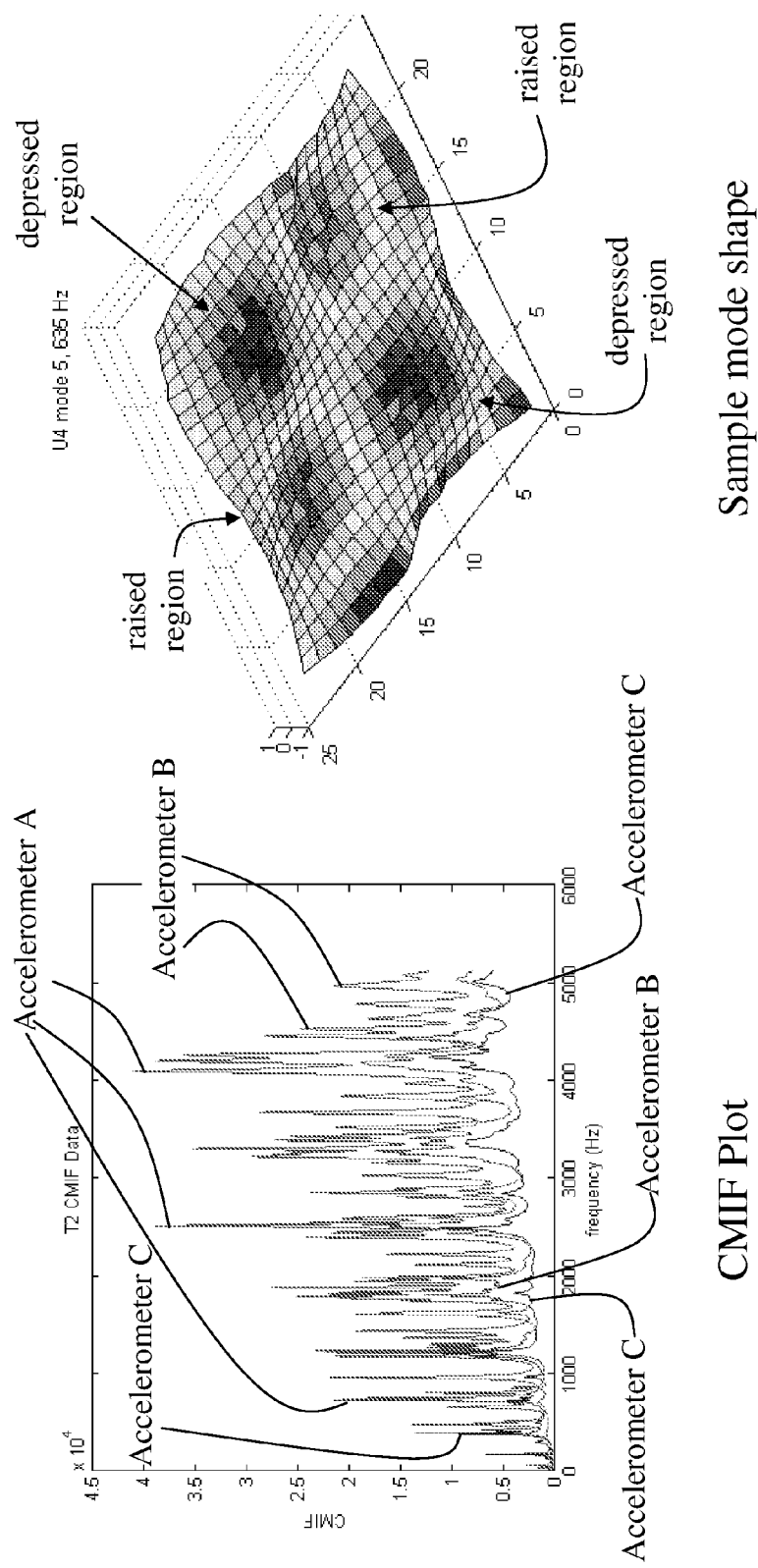
FIG. 16 is a graphical representation of a modal vector analysis of a bonded panel according to one embodiment of the present invention.

Once accelerometers 215 receive vibrational data from the vibrational excitation of panel 200, such as vibrations caused by bimodal hammer 210, a modal analysis of the data is performed. For example, a Complex Mode Indicator Function (CMIF) analysis of the data gathered by the one or more accelerometers 215 may be performed. The left diagram depicted in FIG. 16 shows the results of a CMIF analysis of the data collected by the three accelerometers 215. Each of the peaks in the CMIF plot represents a response mode of panel 200 for a particular vibrational excitation of panel 200.

Each frequency response mode represents a particular modal response of the panel 200. For example, a graphical depiction of the mode shape for the 635 Hz modal response depicted in the left diagram of FIG. 16 is depicted in the right diagram in FIG. 16. The X and Y axes of the sample mode shape diagram represent the 22×22 grid described with respect to FIG. 15.

After performing the CMIF analysis, the modal vectors are matched up with all of the tests performed at each of the 484 locations and the modes are compared across all tests. In embodiments where testing is performed at one or more points (such as at each of the 484 points on panel 200) using two distinct excitation amplitudes (e.g., a weaker and a stronger impact), the modal vectors for the two distinct excitation amplitudes are compared and information related to the shape, damping and/or stiffness is obtained. For example, in one embodiment the CMIF analysis for the soft impacts and the CMIF analysis for the hard impacts are compared to obtain a phase difference between the two sets. Alternate embodiments can include comparison of the amplitude and/or shape. By taking the dot product of (multiplying) the modal vectors of the soft taps and the hard taps, an indication of the correlation between the hard and soft taps is obtained.

After correlation, the modal shapes may be summed together. In the illustrated embodiment, the modal shapes between approximately 150 and 160 Hz (of which there were 6 identifiable modes in the illustrated embodiment) were summed. However, alternate embodiments conclude the summation of different numbers of modes in different frequency ranges. For example, in one embodiment modes below a threshold value (and in some embodiments all the modes below threshold value) are summed. In certain embodiments the threshold value is approximately 5000 Hz, while in alternate embodiments the threshold value is approximately 1000 Hz, while in still other embodiments the threshold value is approximately 650 Hz. In still other embodiments, modes occurring at very low frequencies (for example, below 100 Hz) are not evaluated.

Locations of weak correlation tend to indicate weak bonding between the layers of the laminate material, one example material being panel 200. A difference in the mode response tends to indicate a location of weak bonding within the panel. The damage to the panel (manifesting as weak bonding) changes the response characteristics of the panel and can be detected using embodiments of the present invention.

Figure 17:
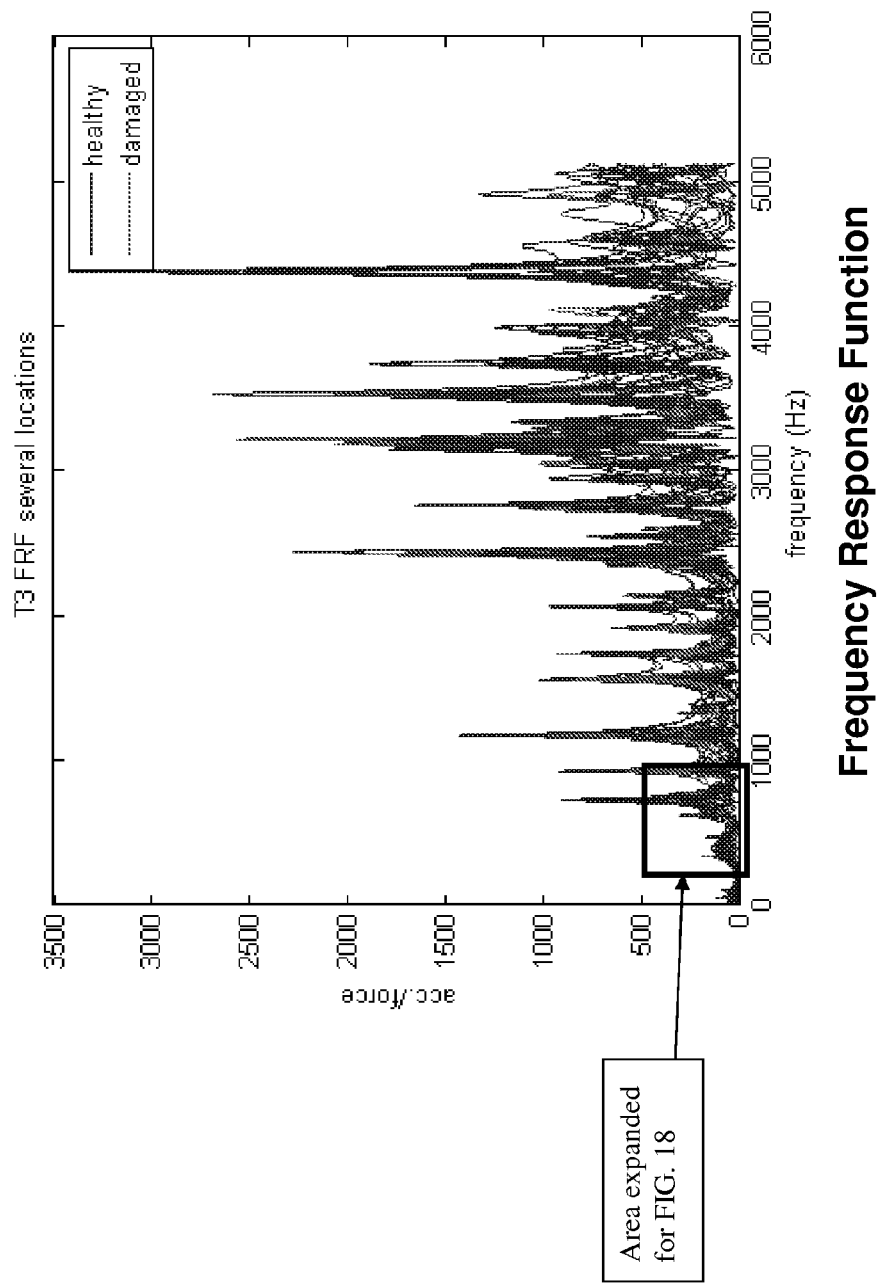
FIG. 17 is a graphical representation of the FRF's from several locations of a bonded panel according to one embodiment of the present invention.
Figure 18:
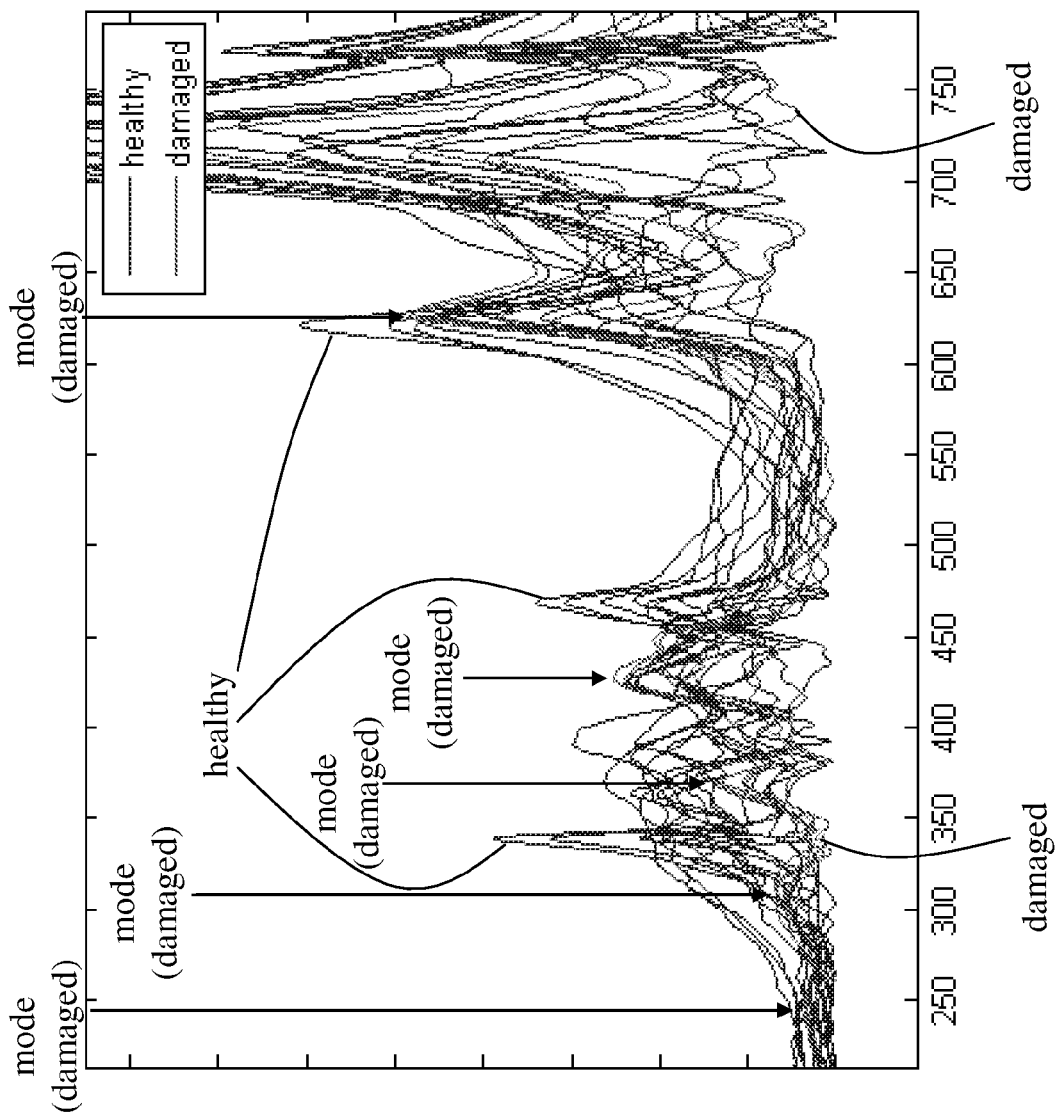
FIG. 18 is an expanded view of a portion of FIG. 17.

FIGS. 17 and 18 depict the overlay of several frequency response functions obtained from impacts at various locations on panel 200. FIG. 17 depicts the frequency response functions between 0 Hz and 6,000 Hz, while FIG. 18 shows an expanded view of the frequency response functions between 200 Hz and 800 Hz. As best be seen in FIG. 18, there is a subset of the data with modes that do not precisely align with the rest of the data, and these modes correlate to vibrational excitations in the regions of weak bonding, i.e., the "damaged" regions. As reflected in FIG. 18, modes (peaks) for the damaged areas occur at approximately 240, 310, 370, 425 and 630 Hz. The modes correlating to lower frequencies appear to more clearly differentiate between the damaged and healthy regions. With respect to panel 200, tested these differences appear greatest between approximately 150 Hz and approximately 650 Hz.

In certain embodiments, the phase of the modal vectors of the frequency response is evaluated at one or more points. In embodiments where testing is performed at one or more points (such as at each of the 484 points on panel 200) using two distinct excitation amplitudes (e.g., a weaker and a stronger impact), the modal parameters of the frequency response for each vibrational amplitude of the one or more points may be compared. In one example embodiment, a Coordinate Modal Assurance Criterion (COMAC) analysis is performed for one or more points. In embodiments where testing is performed at one or more points using two distinct excitation amplitudes, mismatches between the mode shapes in the low and high amplitude excitations can indicate areas of weakened bonding.

Figure 19:
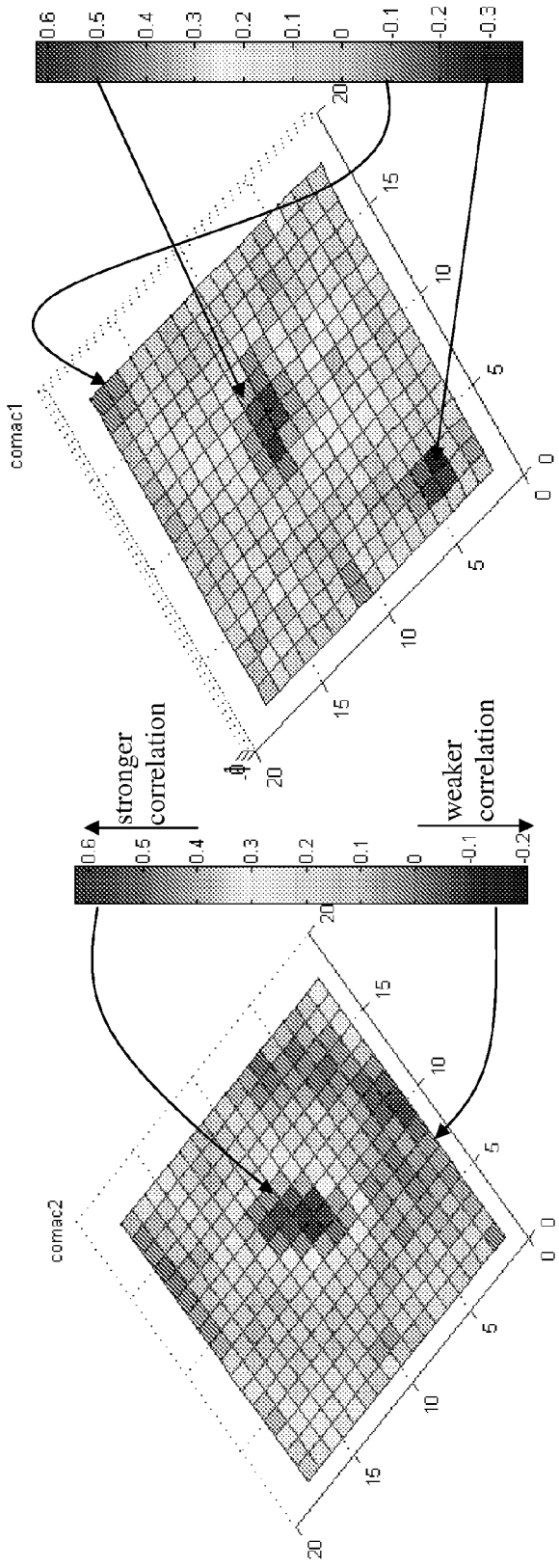
FIG. 19 presents graphical representations of COMAC as a function of location on two healthy panels (Panels 1 and 2) according to an embodiment of the present invention.
Figure 20:
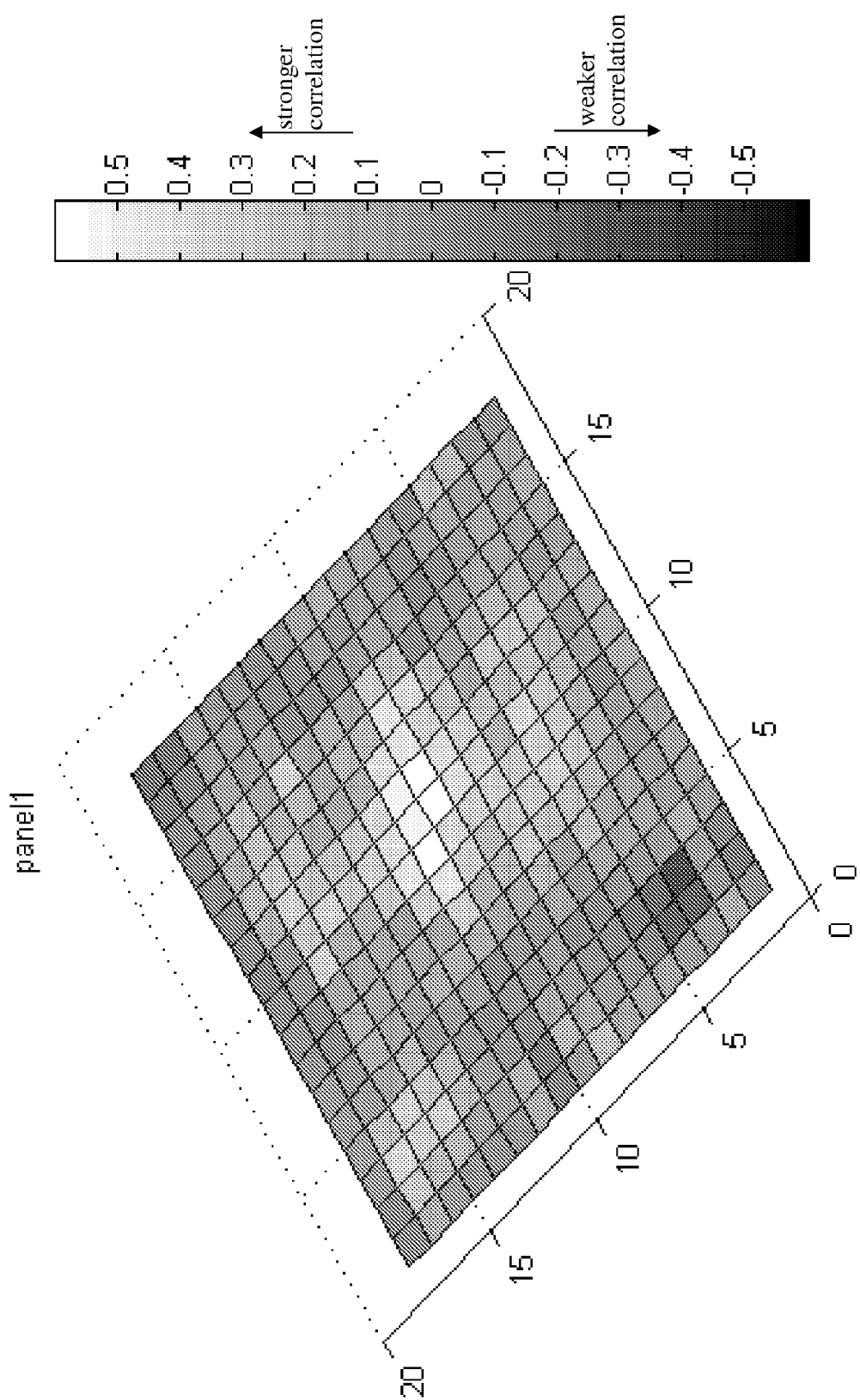
FIG. 20 is an alternate presentation of the COMAC for Panel 1 of FIG. 19.
Figure 21:
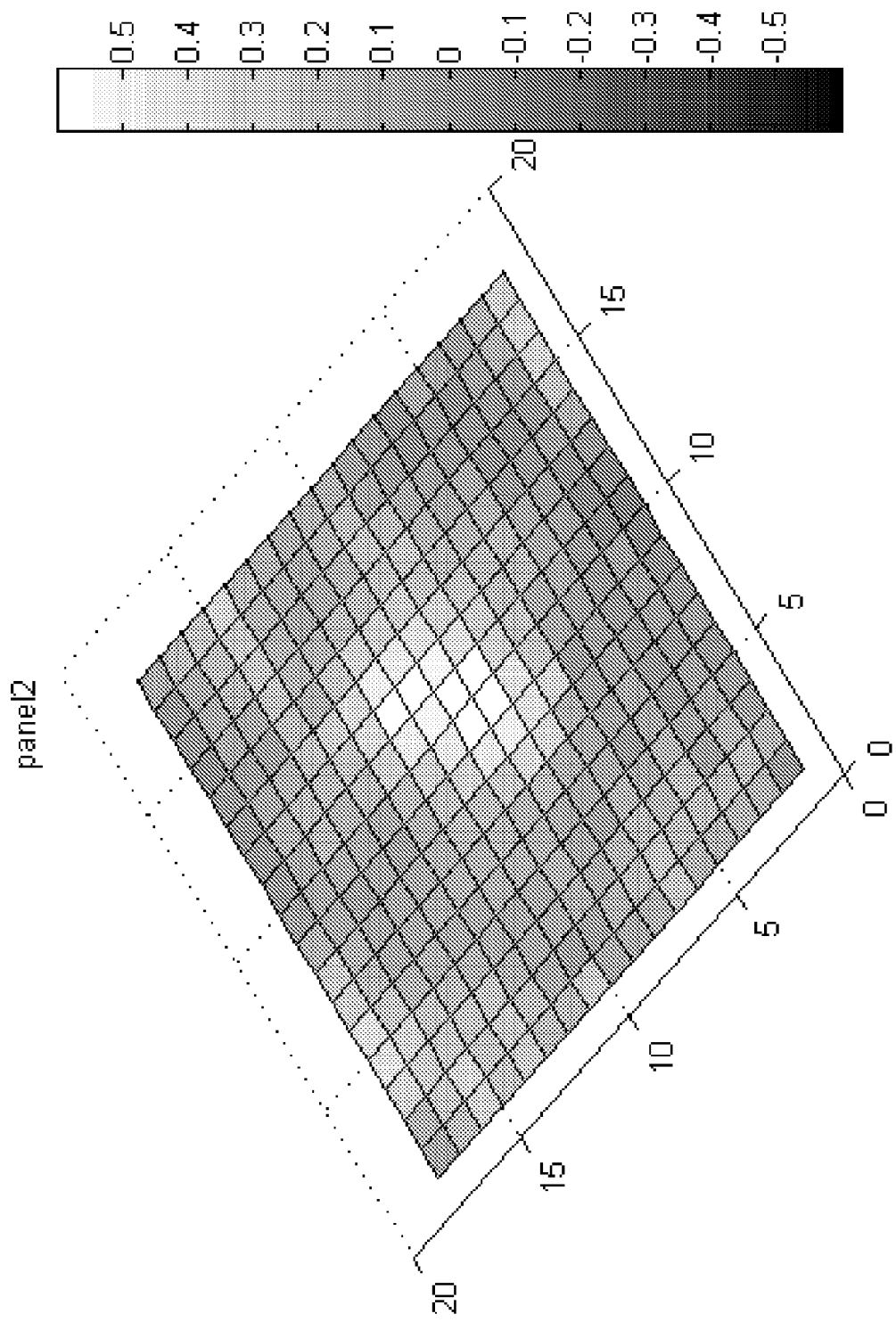
FIG. 21 is an alternate presentation of the COMAC for Panel 2 of FIG. 19.

Depicted in FIGS. 19-21 are the results of performing COMAC analysis on undamaged ("control") panels. In certain embodiments, the analysis of one or more undamaged panels is compared to the analysis of panels in which the state of damage is unknown in order to determine whether the unknown panels contain areas of weak bonding. The data represented by FIGS. 19-21 depicts the results of impacting a test panel at 484 locations (see, e.g., FIG. 15), each location receiving a relatively soft and relatively hard impact. The COMAC for each point represented in FIG. 19 was obtained using all 8 modes appearing between approximately 150 Hz and 650 Hz, and comparing the results of the two different amplitude levels on the same panel. (The two points around the perimeter of the panel are not depicted in FIGS. 19-21 since these points were very noisy, which may be a result of how the tested panels were supported). The "COMAC 1" diagram represents a first undamaged panel and the "COMAC 2" diagram represents a second undamaged panel. Larger values (e g., 0.6) indicates stronger correlation—a similar response between the modes. Lower values (e.g., −0.2) indicate weaker correlation—different responses between the modes. Perfect correlation would be represented by a value of 1.0. FIG. 20 is a representation of the same information contained in the COMAC 1 diagram in FIG. 19, but represented in a different format with the lighter shading indicating stronger correlation and the darker shading indicating weaker correlation. Similarly, FIG. 21 is a representation of the same information contained in the COMAC 2 diagram of FIG. 19, but represented in a different format with the lighter shading indicating stronger correlation and the darker shading indicating weaker correlation.

Alternate embodiments evaluate the COMAC for one or more locations on a panel, such as a panel where the amount of weak bonding (which may correlate to the level of damage) is unknown. The results of this analysis on the panels with unknown damage may be compared to the results of a similar analysis performed on panels with no known damage, although in other embodiments no such comparison is required or performed.

Figure 23:
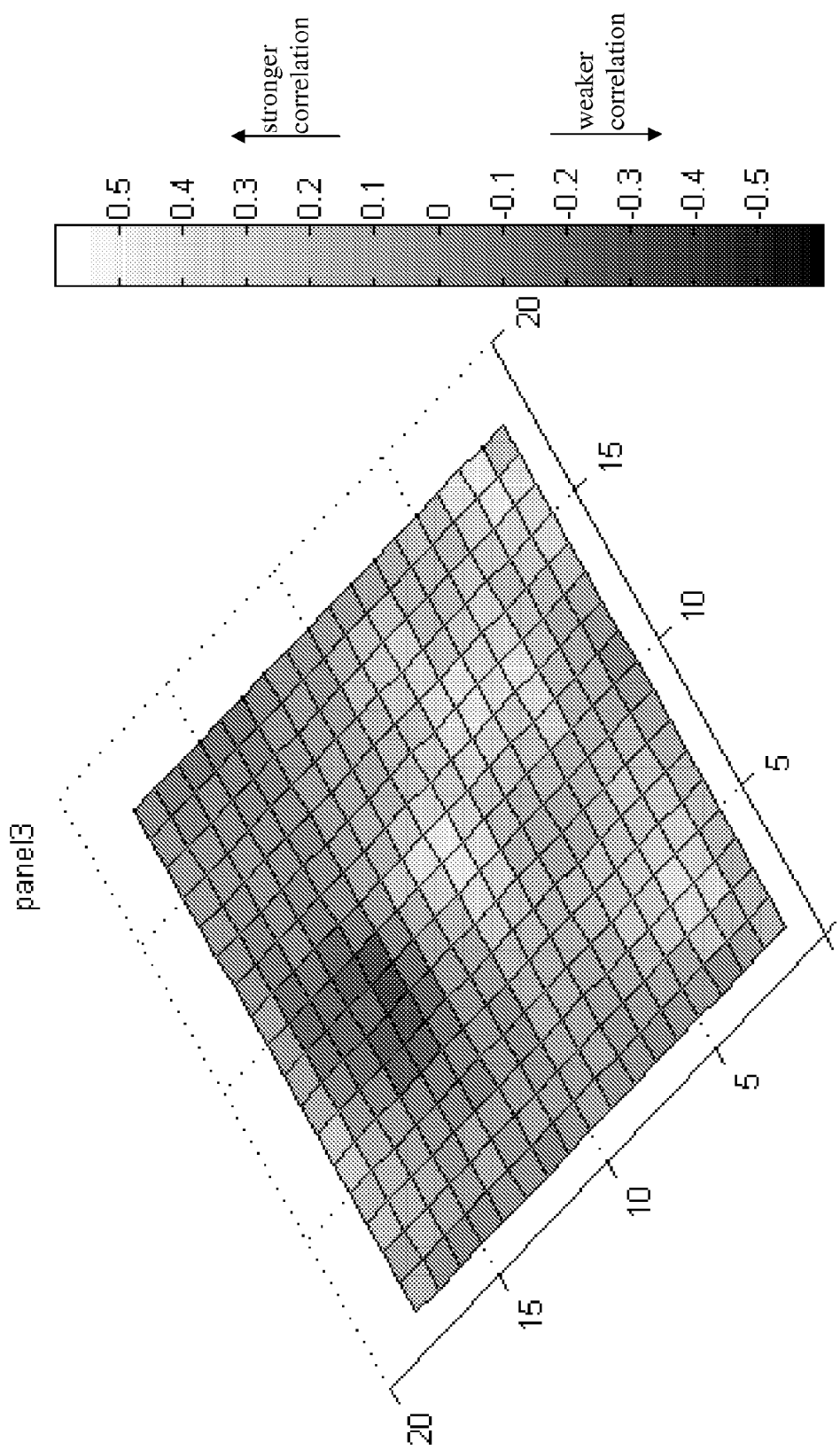
FIG. 23 is an alternate presentation of the COMAC for Panel 3 of FIG. 19.
Figure 24:
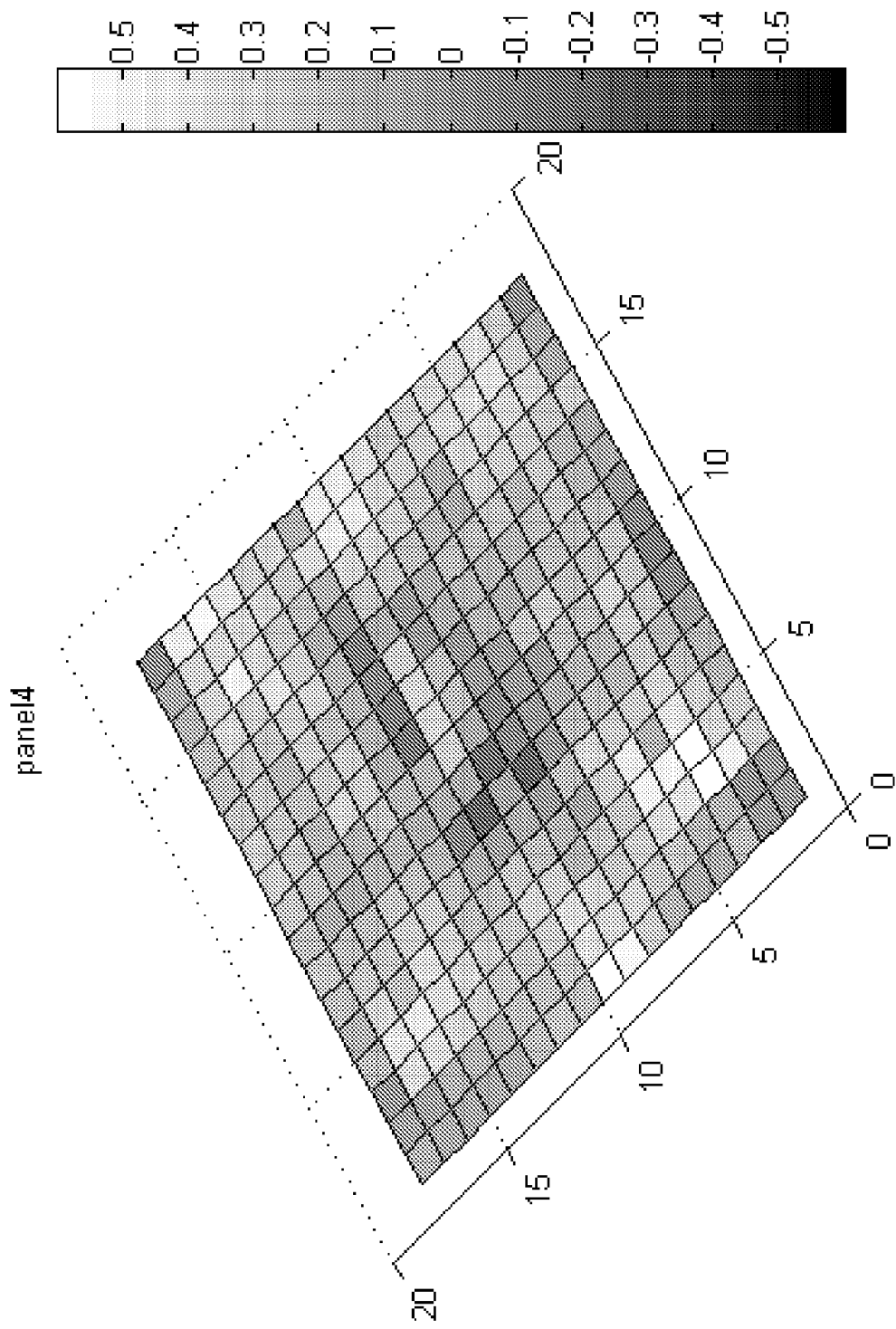
FIG. 24 is an alternate presentation of the COMAC for Panel 4 of FIG. 19.

Depicted in FIGS. 22-24 are the results of COMAC analysis of two panels with known damage, the "damage" to the actual panels being simulated with regions of impaired bonding as described above. (Note that the upper left diagram FIG. 22 is a reproduction of the COMAC 2 diagram depicted in FIG. 19, which reflects the analysis of an undamaged ("control") panel. The squares depicted in the COMAC 3 and COMAC 4 damaged panel results indicate areas of poor correlation, which correspond to the areas of weak bonding on each panel.

FIG. 23 is a different representation of the data contained in the COMAC 3 diagram of FIG. 22 with the lighter shading indicating stronger correlation and the darker shading indicating weaker correlation. Similarly, FIG. 24 is a different representation of the COMAC 4 diagram in FIG. 22, with the lighter shaded regions indicating stronger correlation and the darker shaded regions indicating weaker correlation. As reflected in FIGS. 22-24, the locations of weaker correlation correspond to locations of weak bonding between the panel layers.

In an alternate embodiment, a baseline of COMAC data from a number of known undamaged panels may be obtained, such as by averaging, and added to (or subtracted from) the COMAC data obtained from a panel of unknown damage to identify damaged panels. For example, in some situations the data from a panel of unknown damage, when taken alone, may not clearly indicate areas of weak bonding between the layers. One such example may be represented by the COMAC data for damaged panel 4 in FIGS. 22 and 24. However, when the known baseline of a similar panel with no defects is added to (or subtracted from) the data of panel 4, the damaged area may be more clearly identified.

Figure 25:
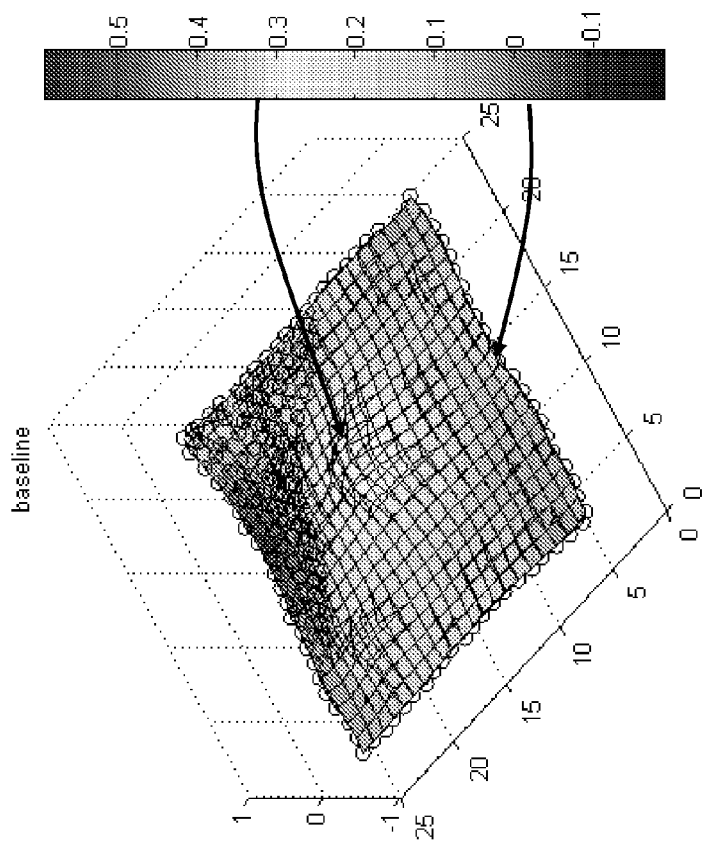
FIG. 25 is a graphical representation of a baseline for approximating a typical healthy panel according to one embodiment of the present invention

FIG. 25 represents an averaging of the COMAC analysis of panels with no known areas of weak bonding (for example, panels 1 and 2 from FIGS. 19-21). The example depicted in FIG. 25 was a baseline that was treated by using a Bezier curve with the average of the baseline panels serving as control points. In alternate embodiments, such as those where the vibrational excitations of the panel are precisely controlled, this baseline analysis may not be required.

Depicted in FIGS. 26-30 are the results of subtracting the baseline information represented by FIG. 25 from the COMAC analysis of panels 1-4 represented in FIGS. 19-24. After the baseline has been subtracted from the results of the COMAC analysis of the undamaged panels (1 and 2), the correlation across the surface of the panel is relatively good indicating little variation between the undamaged panels and the baseline as expected. However, after subtracting the baseline from the COMAC analysis of the damaged panels (3 and 4), the areas of weak correlation are readily identified and are represented by the squares in the two bottom diagrams of FIG. 26.

Figure 26:
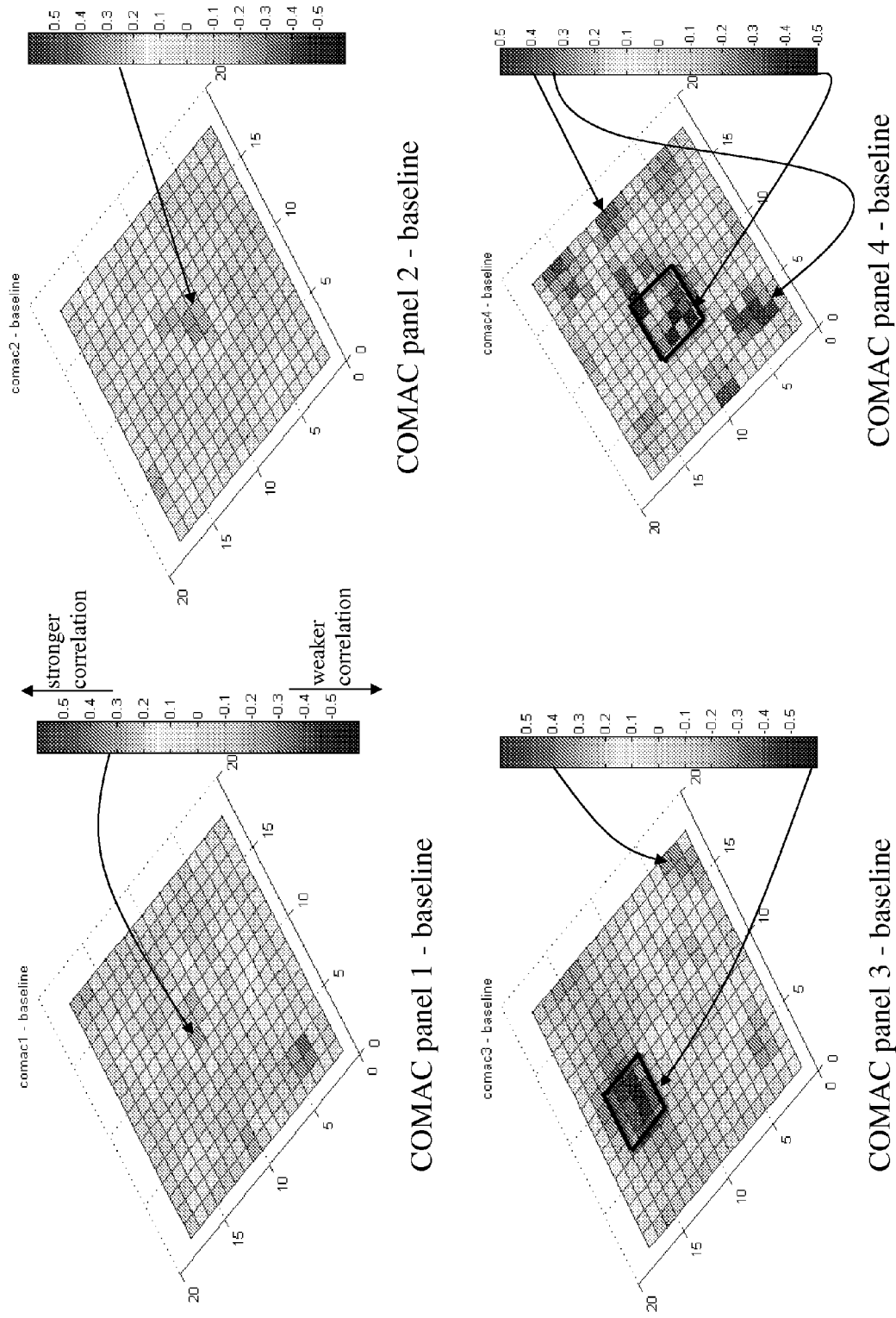
FIG. 26 presents graphical representations of COMAC with the baseline subtracted for two healthy panels (Panels 1 and 2) and two damaged panels (Panels 3 and 4) according to one embodiment of the present invention.
Figure 27:
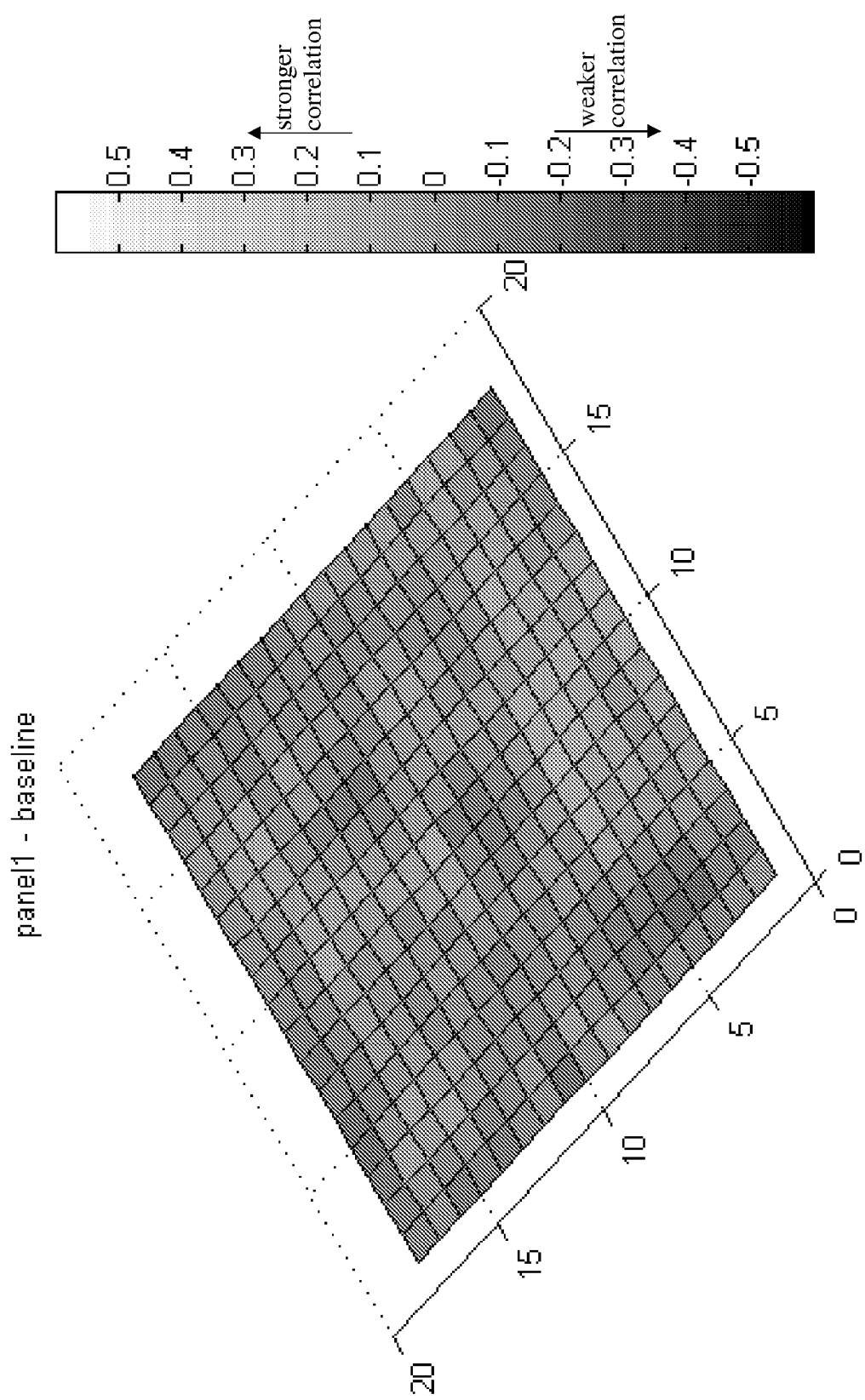
FIG. 27 is an alternate presentation of the FIG. 26 depiction of the COMAC for a healthy panel (Panel 1) with the baseline subtracted.
Figure 28:
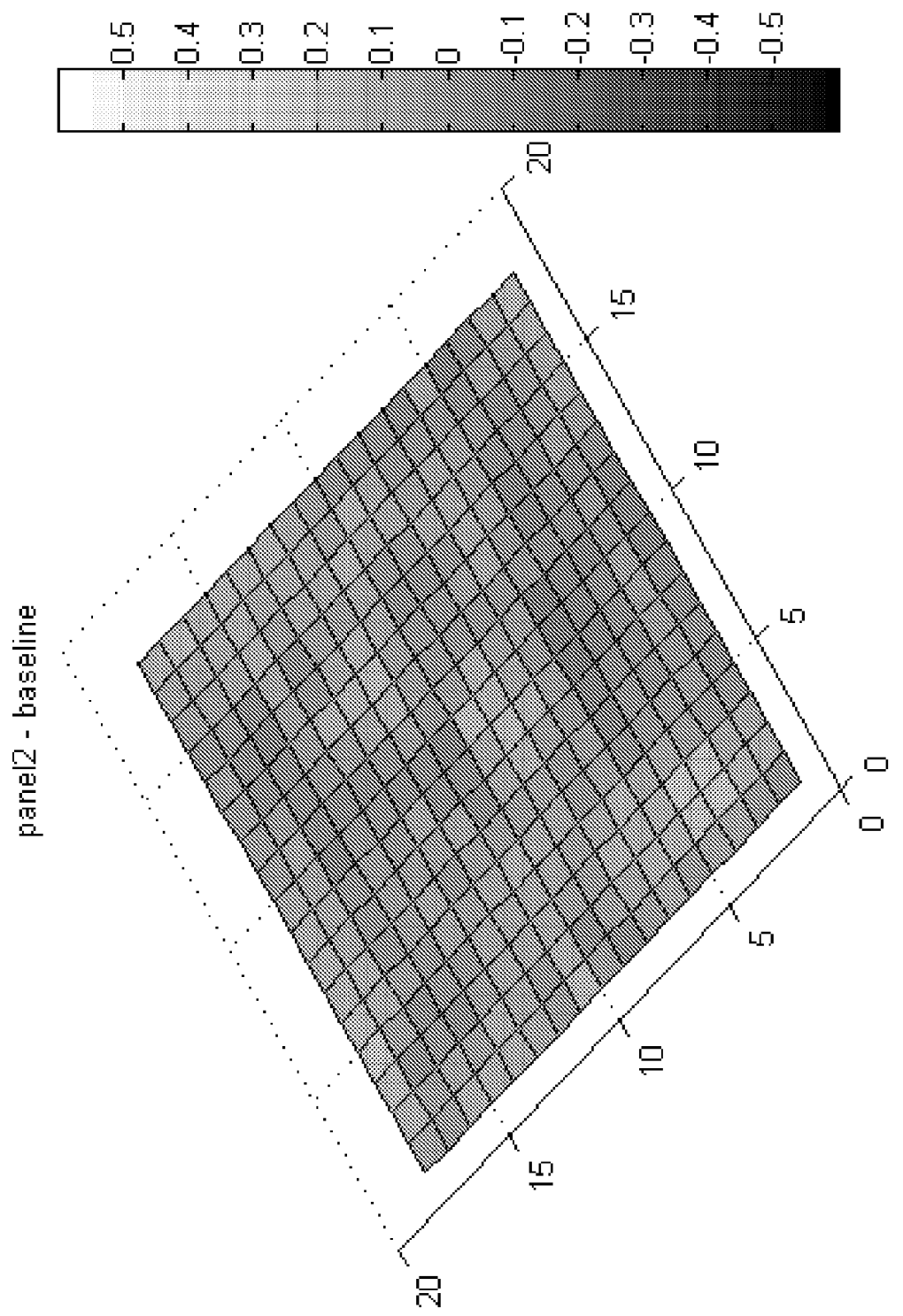
FIG. 28 is an alternate presentation of the FIG. 26 depiction of the COMAC for a healthy panel (Panel 2) with the baseline subtracted.
Figure 29:
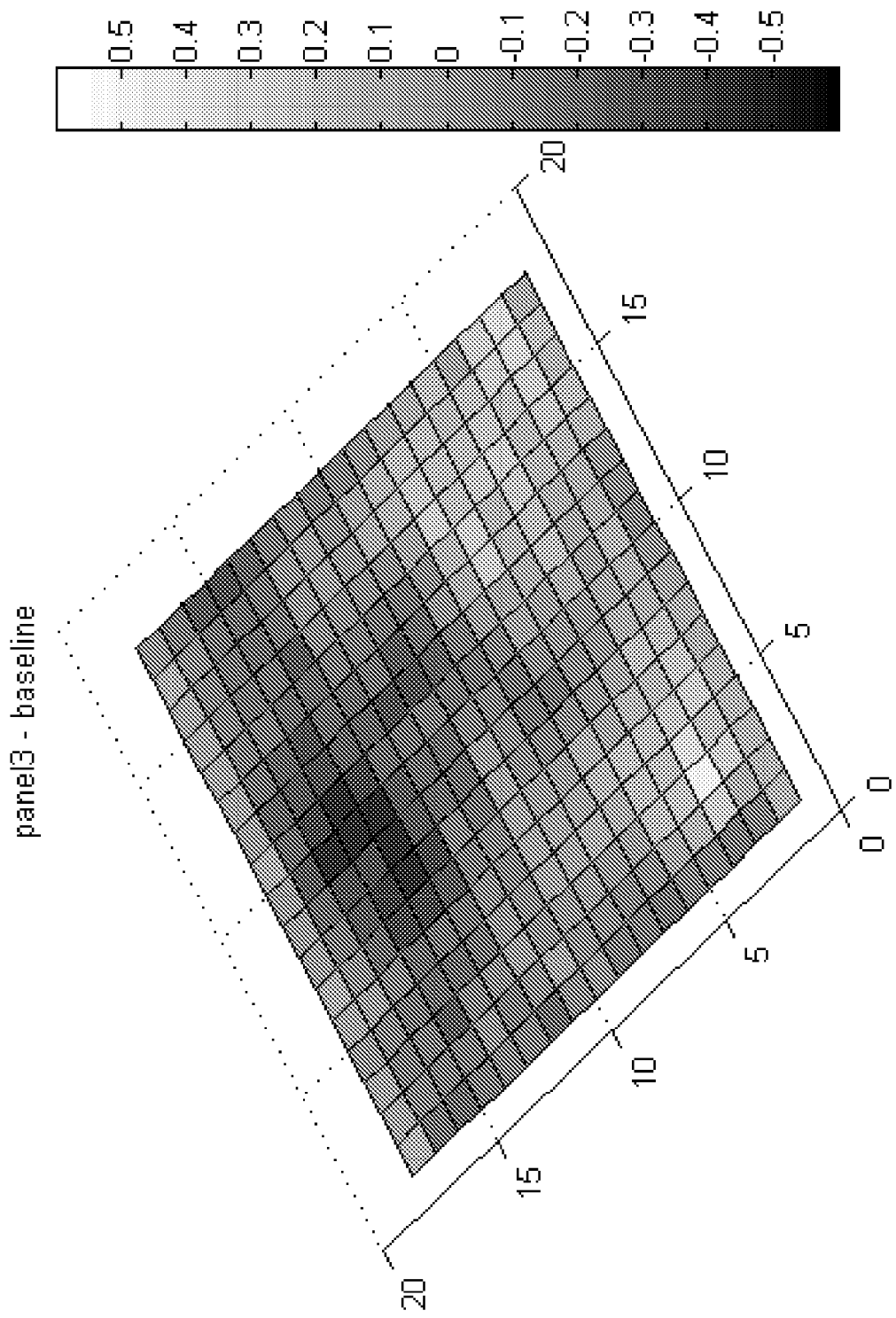
FIG. 29 is an alternate presentation of the FIG. 26 depiction of the COMAC for a damaged panel (Panel 3) with the baseline subtracted.
Figure 30:
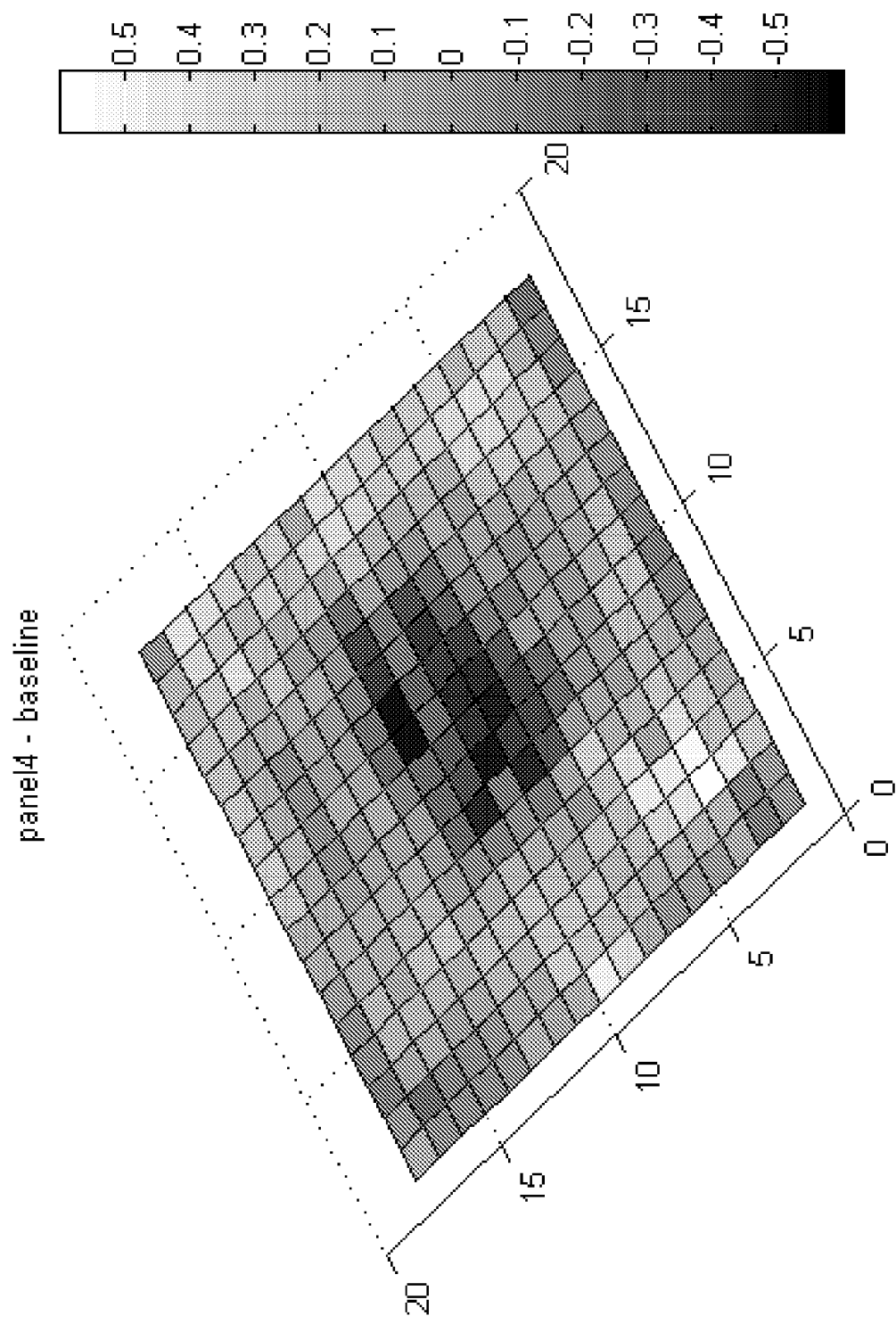
FIG. 30 is an alternate presentation of the FIG. 26 depiction of the COMAC for a damaged panel (Panel 4) with the baseline subtracted.

FIGS. 27-30 present the same information depicted in the diagrams of FIG. 26 with a different representation of the data. For example, FIG. 27 reflects the data in the "COMAC panel 1—baseline" diagram of FIG. 26, but in FIG. 27 the lighter shaded areas indicate stronger correlation while the darker shaded areas indicate weaker correlation. Similarly, FIG. 28 represents the data of the "COMAC panel 2—baseline" diagram in FIG. 26, FIG. 29 represents the "COMAC panel 3—baseline" diagram in FIG. 26, and FIG. 30 represents the "COMAC panel 4—baseline" diagram in FIG. 26, all with the lightly shaded areas indicating regions of stronger correlation and the darker shaded areas indicating regions of weaker correlation.

Computers may be used to process data, such as vibrational data obtained from the accelerometers. The computer, as this example will generically be referred to, generally includes a processor in communication with a memory, an output interface, an input interface, and optionally a network interface. Power, ground, clock, and other signals and circuitry are also typically included.

The processor will typically be a microcontroller or general purpose microprocessor that reads programs from memory. The processor may be comprised of one or more components configured as a single unit. Alternatively, when of a multi-component form, the processor may have one or more components located remotely relative to the others. One or more components of the processor may be of the electronic variety including digital circuitry, analog circuitry, or both. In one embodiment, the processor is of a conventional, integrated circuit microprocessor arrangement, such as one or more CORE 2 QUAD processors from INTEL Corporation of 2200 Mission College Boulevard, Santa Clara, Calif. 95052, USA, or ATHLON or PHENOM processors from Advanced Micro Devices, One AMD Place, Sunnyvale, Calif. 94088, USA, or POWER6 processors from IBM Corporation, 1 New Orchard Road, Armonk, N.Y. 10504, USA. In alternative embodiments, one or more application-specific integrated circuits (ASICs), reduced instruction-set computing (RISC) processors, general-purpose microprocessors, programmable logic arrays, or other devices may be used alone or in combination as will occur to those skilled in the art.

Likewise, the memory in various embodiments includes one or more types such as solid-state electronic memory, magnetic memory, or optical memory, just to name a few. By way of non-limiting example, the memory can include solid-state electronic Random Access Memory (RAM), Sequentially Accessible Memory (SAM) (such as the First-In, First-Out (FIFO) variety or the Last-In First-Out (LIFO) variety), Programmable Read-Only Memory (PROM), Electrically Programmable Read-Only Memory (EPROM), or Electrically Erasable Programmable Read-Only Memory (EEPROM); an optical disc memory (such as a recordable, rewritable, or read-only DVD or CD-ROM); a magnetically encoded hard drive, floppy disk, tape, or cartridge medium; or a plurality and/or combination of these memory types. Also, the memory may be volatile, nonvolatile, or a hybrid combination of volatile and nonvolatile varieties.

While examples, representative embodiments and specific forms of the invention have been illustrated and described in detail in the drawings and foregoing description, the same is to be considered as illustrative and not restrictive or limiting. The description of particular features in one embodiment does not imply that those particular features are necessarily limited to that one embodiment. Features of one embodiment may be used in combination with features of other embodiments as would be understood by one of ordinary skill in the art, whether or not explicitly described as such. Exemplary embodiments have been shown and described, and all changes and modifications that come within the spirit of the invention are desired to be protected.

What is claimed is:

1. A method, comprising the acts of:
   vibrating a structure of bonded layers at a first amplitude by impacting the surface of the structure;
   vibrating the structure at a second amplitude different from the first amplitude by impacting the surface of the structure;
   evaluating a modal response of the structure to said vibrating at a first amplitude;
   evaluating a modal response of the structure to said vibrating at a second amplitude;
   correlating the modal responses; and determining the existence of weak bonding between layers of the structure by identifying a weak correlation between the modal responses.

2. The method of claim 1, wherein said vibrating at first and second amplitudes includes impacting the structure with a modal hammer.

3. The method of claim 1, wherein said vibrating at first and second amplitudes includes vibrating the structure at multiple locations.

4. The method of claim 3, wherein the vibration amplitude at each of the multiple locations is within ten percent (10%) of a target vibration amplitude.

5. The method of claim 3, wherein the multiple locations form a repeating spatial pattern.

6. The method of claim 3, wherein the multiple locations do not form a repeating spatial pattern.

7. The method of claim 3, wherein each of the multiple locations is vibrated at the first and second amplitudes.

8. The method of claim 1, comprising:
evaluating the frequency response for the first and second amplitudes.

9. The method of claim 8, wherein the frequency response of each of the first and second amplitudes includes a modal vector and a phase associated with the modal vector, the method comprising:
evaluating the phase of the modal vectors of the frequency response for the first and second amplitudes.

10. The method of claim 9, comprising:
comparing the modal parameters of the frequency response for the first and second amplitudes.

11. The method of claim 9, wherein said evaluating includes evaluating a Coordinate Modal Assurance Criterion (COMAC) of the frequency response for the first and second amplitudes.

12. The method of claim 1, wherein said evaluating includes comparing the modal responses at frequencies less than 1,000 Hz.

13. The method of claim 1, wherein said evaluating includes comparing the modal responses at frequencies equal to at least 150 Hz and at most 650 Hz.

14. The method of claim 1, wherein said evaluating includes performing a Complex Mode Indicator Function (CMIF) analysis of the modal response.

15. The method of claim 1, wherein said evaluating includes performing a Complex Mode Indicator Function (CMIF) analysis of the frequency response.

16. The method of claim 1, wherein said evaluating includes comparing the modal response to the modal response of a structure with no known weak bonding.

17. The method of claim 1, wherein said evaluating includes creating a baseline modal response for a structure with no known weak bonding; and combining the baseline modal response with the modal response of the structure being evaluated.

18. The method of claim 1, wherein said evaluating includes determining the locations where the modal response of the structure being evaluated differs from the modal response of a structure with no known weak bonding.

19. The method of claim 1, wherein said evaluating includes evaluating the Coordinate Modal Assurance Criterion (COMAC) of the frequency response.

20. The method of claim 19, wherein said evaluating the COMAC is performed for at least two separate modal points located between 150 Hz and 650 Hz inclusive.

21. The method of claim 1, wherein said determining includes determining the location of the weak bonding by identifying a location of weak correlation between the modal responses.

22. The method of claim 21, wherein said determining includes determining the location of the weak bonding within one centimeter (1 cm).

23. The method of claim 1, further comprising:
sensing the response of the structure to said vibrating.

24. The method of claim 23, wherein said sensing is accomplished by at least one accelerometer.

25. The method of claim 24, wherein the at least one accelerometer is a single axis accelerometer.

26. The method of claim 24, wherein the at least one accelerometer is a multiple axis accelerometer.

27. The method of claim 23, wherein said sensing is accomplished by at least three accelerometers.

* * * * *